(12) United States Patent
Slavin et al.

(10) Patent No.: US 11,348,434 B1
(45) Date of Patent: May 31, 2022

(54) SAFETY MONITORING PLATFORM

(71) Applicant: Alarm.com Incorporated, Tysons, VA (US)

(72) Inventors: Alison Jane Slavin, Falls Church, VA (US); Aaron Lee Roberts, Centreville, VA (US)

(73) Assignee: Alarm.com Incorporated, Tysons, VA (US)

( * ) Notice: Subject to any disclaimer, the term of this patent is extended or adjusted under 35 U.S.C. 154(b) by 118 days.

(21) Appl. No.: 16/803,064

(22) Filed: Feb. 27, 2020

Related U.S. Application Data

(63) Continuation of application No. 15/843,437, filed on Dec. 15, 2017, now Pat. No. 10,586,437, which is a
(Continued)

(51) Int. Cl.
*G08B 21/04* (2006.01)
*A61B 5/00* (2006.01)
(Continued)

(52) U.S. Cl.
CPC .......... *G08B 21/0453* (2013.01); *A61B 5/002* (2013.01); *A61B 5/0022* (2013.01); *A61B 5/0024* (2013.01); *A61B 5/0071* (2013.01); *A61B 5/01* (2013.01); *A61B 5/02055* (2013.01); *A61B 5/1112* (2013.01); *A61B 5/1126* (2013.01); *A61B 5/14542* (2013.01); *A61B 5/443* (2013.01); *A61B 5/681* (2013.01); *A61B 5/7282* (2013.01); *A61B 5/743* (2013.01); *A61B 5/746* (2013.01); *A61B 5/747* (2013.01);
(Continued)

(58) Field of Classification Search
CPC ........... G08B 21/0453; G08B 21/0446; A61B 5/002; A61B 5/0071; A61B 5/001; A61B 5/14542; A61B 5/443; A61B 5/681; H04L 67/306
See application file for complete search history.

(56) References Cited

U.S. PATENT DOCUMENTS 7,289,944 B1 10/2007 Genovese
8,207,858 B2 6/2012 Knopf
(Continued)

FOREIGN PATENT DOCUMENTS

WO 2013142900 10/2013

*Primary Examiner* — Quan Zhen Wang
*Assistant Examiner* — Mancil Littlejohn, Jr.
(74) *Attorney, Agent, or Firm* — Fish & Richardson P.C.

(57) ABSTRACT

In some implementations, a system can transmit communications indicating an occurrence of a particular type of safety incident experienced by a user. Registration information that indicates that a plurality of safety devices of different types are to be registered with the user is initially obtained. Sensor data from the plurality of safety devices of different types are obtained. An occurrence of a particular type of safety incident experienced by the user is then selected from among a plurality of types of safety incidents. The selection may be based at least on the obtained sensor data and the obtained registration information. A communication is then provided to another user to indicate the occurrence of the particular type of safety incident experienced by the user in response to selecting the occurrence of the particular type of safety incident.

20 Claims, 9 Drawing Sheets

Related U.S. Application Data continuation of application No. 15/235,590, filed on Aug. 12, 2016, now Pat. No. 9,852,599.

(60) Provisional application No. 62/205,879, filed on Aug. 17, 2015.

(51) Int. Cl.

| | |
|---|---|
| *H04W 4/029* | (2018.01) |
| *H04W 4/90* | (2018.01) |
| *A61B 7/04* | (2006.01) |
| *A61B 5/01* | (2006.01) |
| *A61B 5/145* | (2006.01) |
| *A61B 5/0205* | (2006.01) |
| *H04L 67/306* | (2022.01) |
| *G08B 25/10* | (2006.01) |
| *G08B 25/01* | (2006.01) |
| *H04W 4/38* | (2018.01) |
| *G08B 31/00* | (2006.01) |
| *A61B 5/11* | (2006.01) |
| *H04W 4/02* | (2018.01) |
| *A61B 5/08* | (2006.01) |
| *A61B 5/024* | (2006.01) |
| *A61B 5/021* | (2006.01) |

(52) U.S. Cl.
CPC .......... *A61B 5/7445* (2013.01); *A61B 5/7465* (2013.01); *A61B 7/04* (2013.01); *G08B 21/043* (2013.01); *G08B 21/0423* (2013.01); *G08B 21/0446* (2013.01); *G08B 25/016* (2013.01); *G08B 25/10* (2013.01); *G08B 31/00* (2013.01); *H04L 67/306* (2013.01); *H04W 4/02* (2013.01); *H04W 4/029* (2018.02); *H04W 4/38* (2018.02); *H04W 4/90* (2018.02); *A61B 5/021* (2013.01); *A61B 5/024* (2013.01); *A61B 5/08* (2013.01); *A61B 5/0816* (2013.01); *A61B 5/6803* (2013.01); *A61B 5/6893* (2013.01); *A61B 2562/0219* (2013.01)

(56) References Cited

U.S. PATENT DOCUMENTS

| | | | |
|---|---|---|---|
| 8,294,580 | B2 | 10/2012 | Witwer |
| 8,314,683 | B2 * | 11/2012 | Pfeffer ................ G08B 25/006 340/7.3 |
| 2004/0100384 | A1 | 5/2004 | Chen |
| 2013/0262857 | A1 | 10/2013 | Neuman |
| 2014/0368601 | A1 | 12/2014 | deCharms |
| 2015/0137972 | A1 * | 5/2015 | Nepo .................... G08B 25/10 340/539.13 |
| 2016/0042644 | A1 * | 2/2016 | Velusamy ............ G08G 1/0116 340/435 |
| 2018/0004211 | A1 * | 1/2018 | Grimm ................ G05D 1/0214 |

* cited by examiner

SAFETY MONITORING PLATFORM

CROSS-REFERENCE TO RELATED APPLICATIONS

This application is a continuation of U.S. application Ser. No. 15/843,437, filed Dec. 15, 2017, now allowed, which is a continuation of U.S. patent application Ser. No. 15/235,590, filed on Aug. 12, 2016, now U.S. Pat. No. 9,852,599, issued Dec. 26, 2017, which claims the benefit of U.S. Provisional Patent Application No. 62/205,879 filed on Aug. 17, 2015, all which are incorporated herein by reference in their entirety.

TECHNICAL FIELD

This disclosure relates to monitoring systems and, for example, portable safety monitoring.

BACKGROUND

Users may use mobile communication devices such as smartphones during emergencies. For example, a user may dial 911 to request emergency assistance during an emergency incident.

SUMMARY

Techniques are described for monitoring safety of users with a monitoring platform. The monitoring platform may receive sensor data from various sensors. The various sensor may include sensors that are wearable or incorporated into objects used by the user. For instance, a user may use a wearable device that measures biometric data of the user, a mobile computing device that tracks a user's location, and a bicycle with an embedded accelerometer that measures movement of the bicycle. The devices and sensors may report the measured data to the monitoring platform and the monitoring platform may receive the measured data and determine whether a safety incident has occurred. For example, the monitoring platform may 1 !receive heart rate information that indicates that a user's blood pressure is rapidly lowering, location information that indicates a user is not moving, and accelerometer data that indicates that a user's bicycle suddenly stopped. In response, the monitoring platform may determine that the user is likely to have had a bicycling accident and be seriously injured. In response to determining that a safety issue has likely occurred, the monitoring platform may notify other users or emergency responders. For example, in response to determining that a user is likely to have had a bicycling accident and be seriously injured, the monitoring platform may transmit data to emergency responders indicating that a user is likely to have had a bicycling accident and be seriously injured, the measured data, a location of the user, and a user profile with a photo of the user and past medical information of the user.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings.

DETAILED DESCRIPTION

Figure 1:
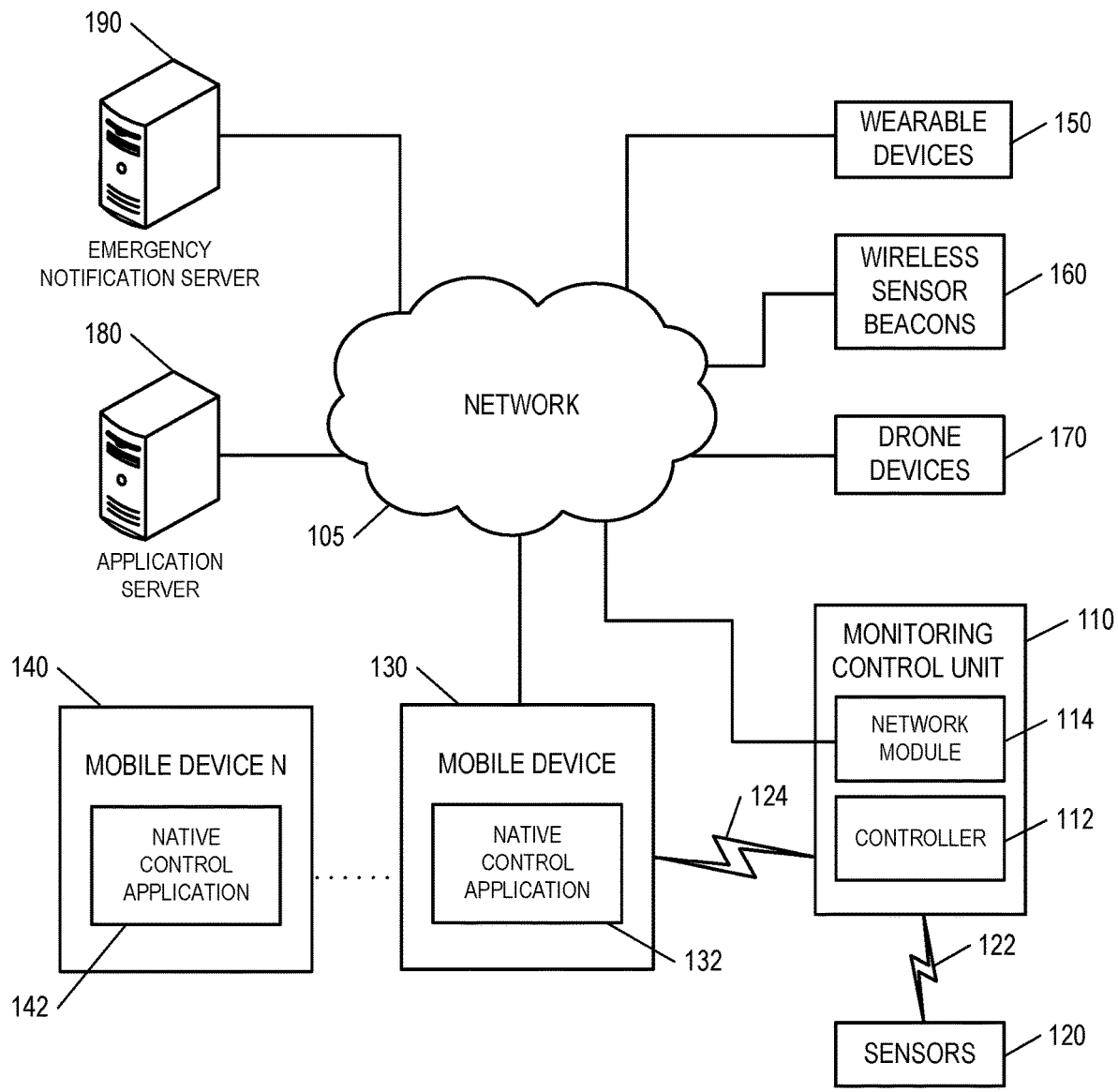
FIG. 1 illustrates an example of a system.

FIG. 1 illustrates an example of a monitoring platform 100 that may be configured to monitor safety of users. The monitoring platform 100 may include a network 105, a monitoring control unit 110, sensors 120, one or more mobile devices 130, 140, wearable devices 150, one or more beacons 160, drone devices 170, an application server 180, and an emergency notification server 190. The network 105 may be configured to enable electronic communications between devices connected to the network 105. For example, the network 105 may be configured to enable exchange of electronic communications between the monitoring control unit 110, the sensors 120, the one or more mobile devices 130, 140, the wearable devices 150, the one or more beacons 160, the drone devices 170, the application server 180, and the emergency notification server 190.

The network 105 may include, for example, one or more of the Internet, Wide Area Networks (WANs), Local Area Networks (LANs), e.g., Wi-Fi, analog or digital wired and wireless telephone networks, e.g., a public switched telephone network (PSTN), Integrated Services Digital Network (ISDN), a cellular network, and Digital Subscriber Line (DSL), Ethernet, Internet Protocol (IP) over broadband, radio, television, cable, satellite, or any other delivery or tunneling mechanism for carrying data. The network 105 may include multiple networks or subnetworks, each of which may include, for example, a wired or wireless data pathway. The network 105 may also include a circuit-switched network, a packet-switched data network, or any other network able to carry electronic communications (e.g., data or voice communications). For example, the network 105 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 105 may include one or more networks that include wireless data channels and wireless voice channels. The network 105 may also be a wireless network, a broadband network, or a combination of networks including a wireless network and a broadband network.

The monitoring control unit 110 may include a controller 112 and a network module 114. The controller 112 may be configured to control a system, e.g., a home security system associated with a property that includes the monitoring control unit 110. In some examples, the controller 112 may include a processor or other control circuitry configured to execute instructions of a program that controls operation of a home security system. In these examples, the controller 112 may be configured to receive input from sensors, detectors, or other devices associated with the home security system, e.g., a motion sensor, a security camera, an occupancy sensor, or a thermostat. For example, the controller 112 may be configured to control operation of the network module 114 included in the monitoring control unit 110.

The network module 114 may be a communication device configured to exchange communications over the network 105. The network module 114 may be a wireless communication module configured to exchange wireless communications over the network 105. For example, the network module 114 may be a wireless communication device configured to exchange communications over a wireless data channel. In this example, the network module 114 may transmit user location data within or external to the property, environmental data from the property, e.g., indoors at the property or outdoors at the property, or other data over a wireless data channel. The wireless communication device may include one or more GSM modules, a radio modem, a cellular transmission module, or any type of module configured to exchange communications in one of the following formats: GSM or GPRS, CDMA, EDGE or EGPRS, EV-DO or EVDO, UMTS, or IP.

The network module 114 also may be a wired communication module configured to exchange communications over the network 105 using a wired connection. For instance, the network module 114 may be a modem, a network interface card, or another type of network interface device. The network module 114 may be an Ethernet network card configured to enable the monitoring control unit 110 to communicate over a local area network and/or the Internet. The network module 114 also may be a voiceband modem configured to enable the alarm panel to communicate over the telephone lines of Plain Old Telephone Systems (POTS). In some implementations, the alarm panel may be a broadband or cellular gateway where the network module 114 may enable the monitoring control unit 110 to communicate over the network 105.

The sensors 120 may include cameras, pressure sensors, temperature sensors, motion sensors, occupancy sensors, or device sensors that may communicate with the monitoring control unit 110 over the communication link 122. For example, the sensors 120 may provide the monitoring control unit 110 sensor data indicating when users left a home, when users arrived home, what users are home, what users were doing before they left the home and an appearance of users when they left the home.

In other implementations, the sensors 120 may include motion sensors, pressure sensors, or other sensors that determine occupancy and usage of appliances/features within the property. For example, in one instance, motion and temperature sensors may be placed on the walls within a room to determine if a person is currently occupying or not occupying the room. In another instance, the sensors 120 may be placed on particular objects and/or appliances to monitor user activity and user safety within a property. For example, touch sensors may be placed on common appliances such as, for e.g., an oven, a stove, a blender, a space heater, which may cause personal injuries to users. In some implementations, the sensors 120 within the property may collect user activity data based on proximity with the wearable devices 150 to track user movement within the property. In another example, the sensors 120 may only collect user activity data when the user is located within property based on location data transmitted from the wearable devices 150 indicating that the user is within a particular distance (e.g., 5 meters) from the sensors 120.

The one or more mobile devices 130, 140 may be devices that host one or more native applications, e.g., the native applications 132, 142. The one or more mobile devices 130, 140 may be cellular phones or non-cellular locally networked devices. The one or more mobile devices 130, 140 may include a cell phone, a smart phone, a tablet PC, a personal digital assistant ("PDA"), or any other portable device configured to communicate over a network. For example, implementations also may include portable music players, other communication devices, and handheld or portable electronic devices for gaming, communications, and/or data organization. The one or more mobile devices 130, 140 may be the same or may include mobile devices of different types. The one or more mobile devices 130, 140 may perform functions unrelated to the monitoring platform 100, such as placing personal telephone calls, playing music, playing video, displaying pictures, browsing the Internet, maintaining an electronic calendar, etc.

In some implementations, the one or more mobile devices 130, 140 may communicate with and receive data from the monitoring control unit 110 using the communication link 124. For instance, the one or more mobile devices 130, 140 may communicate with the monitoring control unit 110 using various local wireless protocols, such as Wi-Fi, Bluetooth, Z-Wave, ZigBee, HomePlug (Ethernet over power line), or wired protocols such as Ethernet, USB, and other wired protocols based on the RS232, RS485, and/or RS422 standards. The one or more mobile devices 130, 140 may connect locally to the monitoring platform 100, its sensors, and other devices. The local connection may improve the speed of communications because communicating through the network 105 with a remote server, e.g., the application server 180, may be slower.

Although the one or more mobile devices 130, 140 are shown communicating with the monitoring control unit 110, the one or more mobile devices 130, 140 may communicate directly with the sensors 120, the wearable devices 150, the beacons 160, the drone devices 170, and other devices controlled by the monitoring control unit 110. In some implementations, the one or more mobile devices 130, 140 may replace the monitoring control unit 110 and perform the functions of the monitoring control unit 110 for local control and long range or offsite communication.

In other implementations, the one or more mobile devices 130, 140 may receive data captured by the monitoring control unit 110 through the network 105. The one or more mobile devices 130, 140 may receive the data from the monitoring control unit 110 through the network 105 or the application server 180 and may relay data received from the monitoring control unit 110 to the one or more mobile devices 130, 140 through the network 105. In this regard, the application server 180 may facilitate communications between the one or more mobile devices 130, 140 and the monitoring control unit 110.

Although the one or more mobile devices 130, 140 are shown in FIG. 1 as being connected to the network 105, in some implementations, the one or more mobile devices 130, 140 are not connected to the network 105. In these implementations, the one or more mobile devices 130, 140 may communicate directly with one or more of the monitoring platform 100 components and no network connection, e.g., connection to the Internet, or reliance on remote servers is needed.

In some implementations, a mobile device 130, 140 may be able to determine a geographic location associated with the mobile device 130, 140, and may communicate information identifying a geographic location associated with the mobile device 130, 140 to the sensors 120 or the wearable devices 150. For example, a mobile device 130, 140 may determine the current geographic location of the mobile device 130, 140 by using global positioning system (GPS) capabilities. In other implementations, a geographic location associated with a mobiles device 130, 140 may be determined using other methods, for example, by using Wi-Fi access point triangulation data, cellular network triangulation data, or IP address information, when the mobile device 130, 140 has network connectivity. The mobile device 130, 140 may additionally or alternatively transmit data identifying the geographic location of the mobile device 130, 140 over the network 105 to the application server 180, or to the monitoring control unit 110.

Figure 2A:
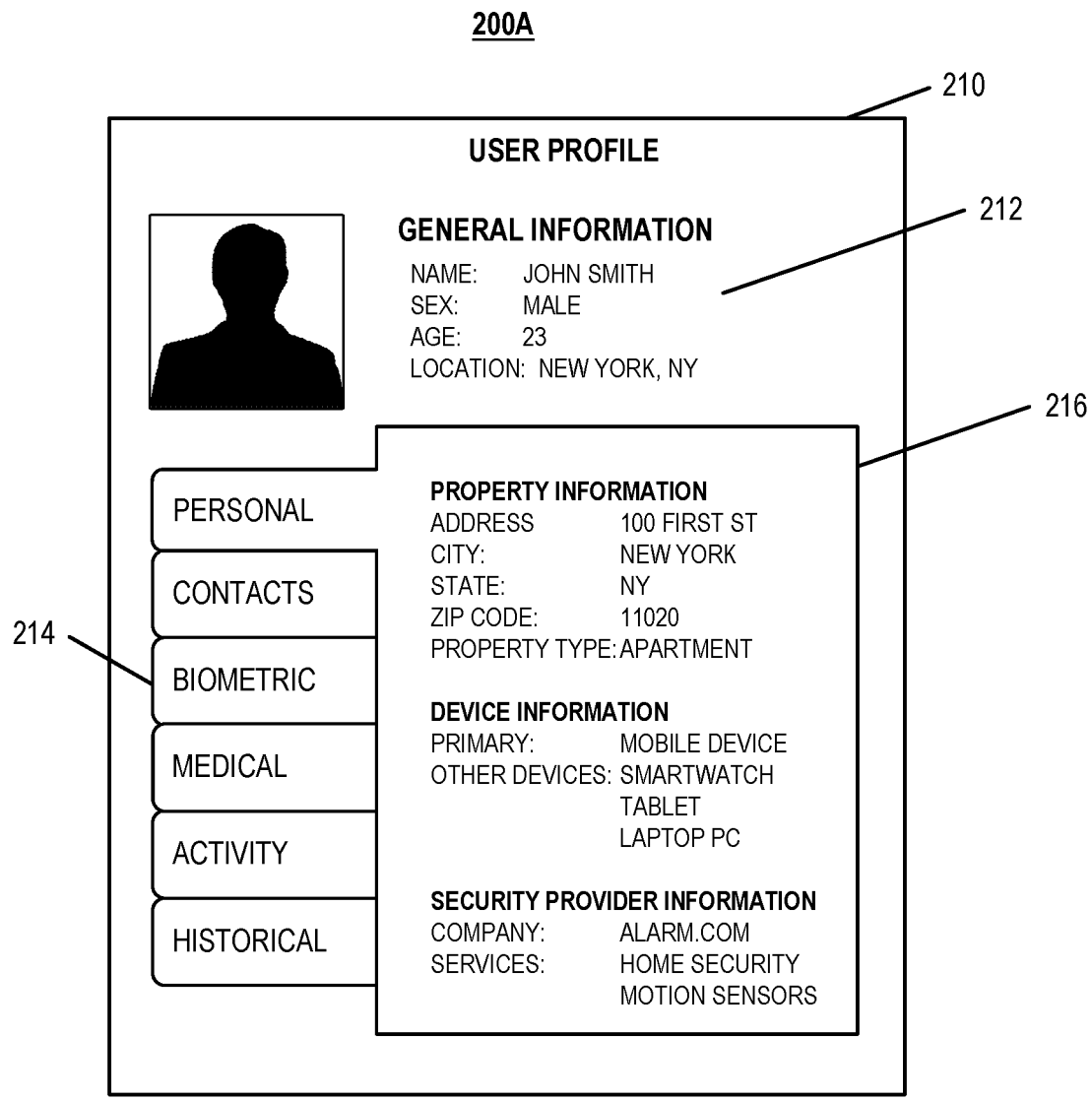
FIGS. 2A-2C illustrate examples of user interfaces in a safety monitoring platform.
Figure 2B:
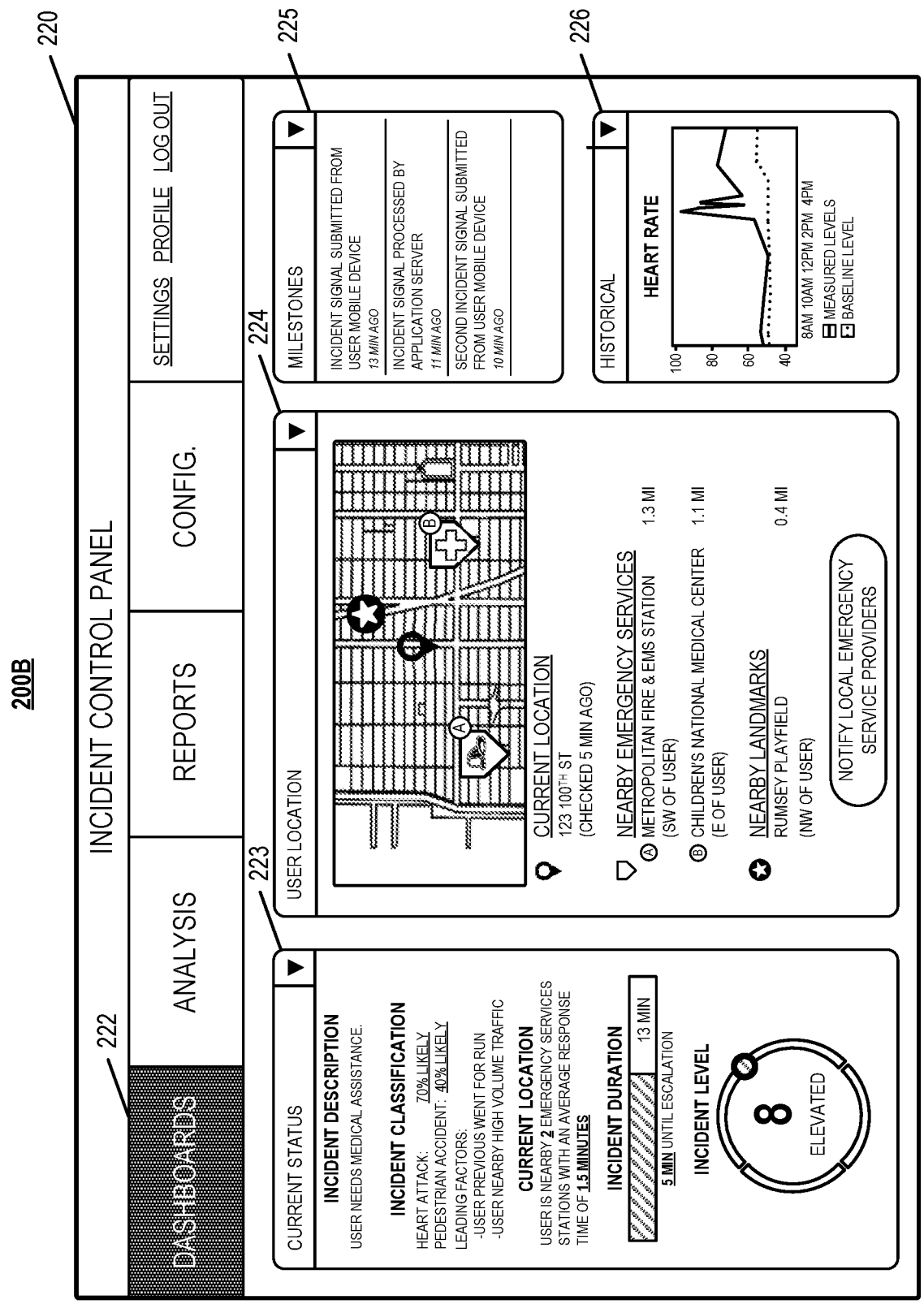
Figure 2C:
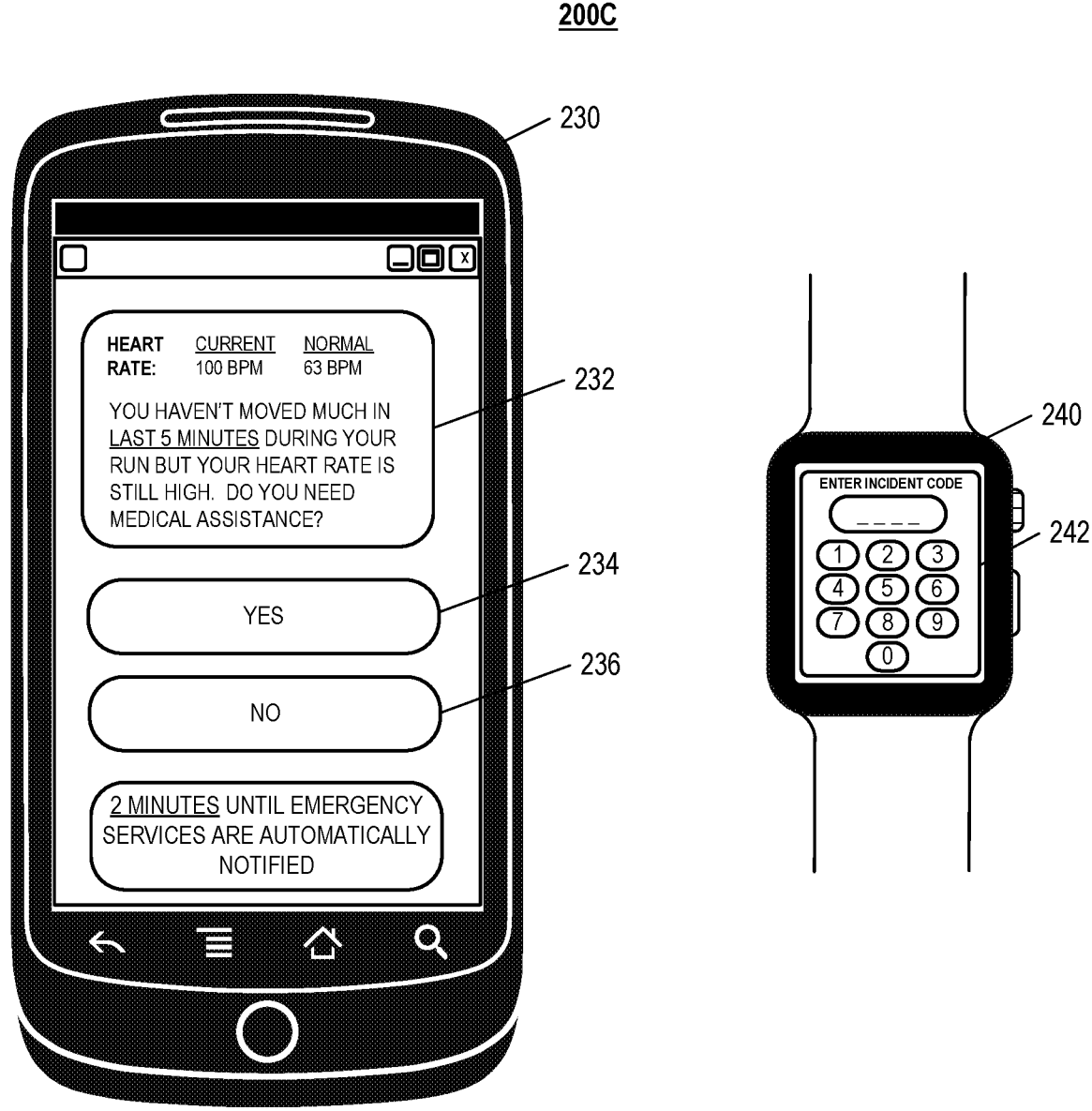

The one or more mobile devices 130, 140 may each include a native applications 132, 142, respectively, as represented more particularly in FIGS. 2A-2C. The native applications 132, 142 refers to a software/firmware program running on the corresponding mobile devices that enables the safety monitoring features described within this disclosure. The one or more mobile devices 130, 140 may load or install the native applications 132, 142 based on data received over a network or data received from local media. The native monitoring applications 132, 142 may run on mobile devices' platforms, such as Apple iOS, iPhone, iPod touch, Blackberry, Google Android, Windows Mobile, etc.

The native applications 132, 142 identifies and displays user data such as, for e.g., a geographic location associated with the mobile device 132, 142 and communicates information identifying the geographic location to various devices within the monitoring platform 100 such the sensors 120, the wearable devices 150, or the monitoring control unit 110. In some instances, the native applications 132, 142 may also transmit user data to the application server 180. For example, a mobile device 130, 140 having the native application 132, 142 may determine a geographic location of the mobile device 130, 140 using GPS capabilities, and may communicate data identifying the geographic location to the application server 180. In some instances, the native application 132, 142 may check the location of the mobile device 130, 140 periodically and may automatically detect when a user associated with the mobile device 130, 140 is going toward or away from a property.

The wearable devices 150 may be portable electronic devices that may be incorporated into items of clothing and accessories worn by a user. The wearable devices 150 may be activity trackers, smartwatches, smart glasses, handhelds, bracelets, necklace pendants, or any wearable device configured to communicate over a network. The wearable devices 150 may include devices of different types. The wearable devices 150 may perform functions unrelated to the monitoring platform 100, such as monitoring user activity data such as, for e.g., biometric data, fitness data, sleep data, user-inputted data, and any other type of quantitative data.

In some implementations, the wearable devices 150 may include an integrated panic button that a user may push to have the wearable devices 150 transmit a distress signal indicating that the user requires emergency assistance to either the application server 180 or the emergency notification server 190.

In some implementations, the wearable devices 150 may include embedded sensors that measure various biometric data such as, for e.g., heart rate or rhythm, breathing rate, blood oxygen level, blood pressure, skin temperature, skin moisture. In some implementations, the wearable devices 150 may include hardware components such as an accelerometer, a gyroscope, a microphone, a camera, image sensors, video sensors, sound sensors, and/or an automated speech recognizer.

The wearable devices 150 may constantly monitor and process data transmitted between the components of the monitoring platform 100 such as, e.g., the monitoring control unit 110, the sensors 120, or the one or more mobile devices 130, 140.

In some implementations, the wearable devices 150 may function independently of the components of the monitoring platform 100 and include a separate network module that enables the wearable devices 150 to connect to the components of the monitoring platform 100 by exchanging wireless communications over the network 105. For instance, the wearable devices 150 may include one or more GSM modules, a radio modem, a cellular transmission mode, or any type of module configured to exchange communications in the following formats: LTE, GSM or GPRS, CDMA, EDGE, EGPRS, EV-DO or EVDO, UMTS, or IP. In other instances, the wearable devices may be capable of using various local wireless protocols, such as Wi-Fi, ANT, Bluetooth, Z-Wave, ZigBee, HomePlug (Ethernet over powerline), or wired protocols such as Ethernet, USB, and other wired protocols based on the RS232, RS485, and/or RS422 standards. For example, the wearable devices 150 may transmit measured data to the one or more mobile devices 130, 140 over a local wireless protocol and the one or more mobile devices 130, 140 may then transmit the data received by the wearable devices 150 to the application server 180.

The one or more wireless sensor beacons 160 can be devices capable of emitting and/or receiving information over a wireless communication channel. For example, the wireless sensor beacons 160 may utilize Bluetooth Low Energy (BLE), also known as Bluetooth Smart, or other wireless technologies such as, for e.g., Wi-Fi, near-field communications (NFC), or other wireless technologies, to communicate with the devices connected over the network 105. The wireless sensor beacons 160 may be commercially available beacon devices or other types of beacon devices. The wireless sensor beacons 160 may communicate with the devices of the monitoring platform 105 by emitting messages (e.g., pings) that include information identifying the wireless sensor beacons 160.

In some implementations, devices of the monitoring platform 100 such as the one or more mobile devices 130, 140, and the wearable devices 150 may communicate with the wireless sensor beacons 160 by receiving message from the one or more wireless sensor beacons 160 identifying one or more of the wireless sensor beacons 160. For example, each of the one or more wireless sensor beacons 160 may be associated with a unique universal identifier (UUID) that identifies a particular wireless sensor beacon within a group of two or more wireless sensor beacons within a particular geographic location, for e.g., a shopping complex.

In some implementations, a particular wireless sensor beacon 160 may be associated with particular regions within a geographic location, for e.g., particular floors or individual shops within a shopping complex, to monitor user data by exchanging communications with nearby one or more mobile devices 130, 140 or wearable devices 150. For example, one or more wireless sensor beacons 160 may be placed within multiple floors of a shopping complex, each with different UUIDs and a particular set of latitude and longitude coordinates that are associated with a defined region (e.g., a section within a store, an outdoor area, a building, a venue or other space).

Each of the one or more wireless sensor beacons 160 may broadcast information to allow the devices of the monitoring platform 100 to recognize the one or more of the wireless sensor beacons 160. In some instances, the one or more wireless sensor beacons 160 broadcast their information periodically for particular periods of time (e.g., every second, every millisecond). The one or more wireless sensor beacons 160 may broadcast this information using wireless communications protocols such as, for e.g., BLE. In some implementations, information broadcasted by the one or more wireless sensor beacons 160 may also be broadcasted on particular frequencies or power levels to control the types of devices on the monitoring platform 100 that receive the information. For example, the one or more wireless sensor beacons 160 may transmit information to the one or more mobile devices 130, 140 and the wearable devices 150, on different frequencies, respectively.

In some implementations, the one or more wireless sensor beacons 160 may be placed in common regions that experience high user traffic volumes such as, for e.g., a public park, a tourist attraction, a public transportation station, a commercial complex, or other types of highly populated locations. In such implementations, the one or more wireless sensor beacons 160 may be configured with third-party electronic transportation or safety platforms to transmit information to the devices connected to the monitoring platform 100. For example, the one or more wireless sensor beacons 160 may detect a hazardous condition on a subway line based on receiving safety signals from the transportation authority and in response, transmit this information to the one or more mobile devices 130, 140 or the wearable devices 150.

In some implementations, the one or more wireless sensor beacons 160 may be configured to operate with a particular mobile application that is installed on the devices connected to the monitoring platform 100. For example, the particular mobile application may include a software development kit (SDK) that enables the devices connected to the monitoring platform to exchange communications with the one or more wireless sensor beacons 160. For instance, the different devices connected to the monitoring platform 100 may independently exchange communications with the one or more wireless sensor beacons 160. In such instances, a wearable device 150 may be able to transmit a distress signal including user data to the one or more wireless sensor beacons without the user having his/her mobile device with him. In other instances, the one or more wireless beacons 160 may receive redundant signal transmissions from the different devices connected to the monitoring platform 100 to ensure that distress signal is adequately transmitted to the application server 180 when one or more of the devices connected to the monitoring platform 100 malfunctions. For example, if a user is involved in a car crash that destroys his/her wearable device and mobile device, the monitoring platform 100 may determine that these devices are unable to transmit the distress signal and instead transmit a distress signal including cached data stored on other devices connected to the monitoring platform 100 such as the one or more wireless sensor beacon 160 or the drone devices 170.

In some implementations, the one or more wireless sensor beacons 160 may be connected to emergency call booths that enable the one or more wireless sensor beacons 160 to identify devices within a particular distance (e.g., 30 meters) when the devices transmit a distress signal to the monitoring platform 100. For example, the emergency call booths may monitor a particular frequency that includes the frequency of the outgoing distress signals transmitted by nearby devices. In response to detecting that a nearby device has transmitted a distress signal within a particular time period (e.g., 5 minutes), the particular wireless sensor beacon 160 that is connected to the emergency call may then transmit a signal including location information to the emergency notification server 190.

The drone devices 170 may be an unmanned device that is capable of movement. For example, the drone devices 170 may be capable of moving throughout a location based on automated control technology and/or user input control provided by either the user or by the devices connected to the monitoring platform 100. In this example, the drone devices 170 may be able to fly, roll, walk, or otherwise move about a location. The drone devices 170 may include helicopter type devices (e.g., quad copters), rolling helicopter type devices (e.g., roller copter devices that can fly and also roll along the grounds, walls, or ceiling), land vehicle type devices (e.g., automated cars that drive around a property), and plane type devices (e.g., unmanned aircraft).

In some implementations, the drone devices 170 may be dispatched in response to an incident signal indicating that a user may require emergency assistance. For example, if a user has been injured during a known running route, the wearable device 150 may transmit data to the application server 180 from which the application server 180 may determine there is a likely safety incident, and in response, transmit an incident signal and a location of the user to the emergency notification server 190 and also transmit a dispatch instruction with the user location to the drone devices 170. The application server 180 may determine the location of the user during an incident based on comparing current data collected by the sensors 120, one or more mobile devices 130, 140, the wearable device 150, or the one or more wireless sensor beacons 160 to historical information about the user or user activity. In such examples, the monitoring platform 100 may deploy the drone devices 170 to the determined location. In some instances, the drone devices 170 may be equipped with a broadband connection that allows the drone devices 170 to connect with the network 105.

In some implementations, the drone devices 170 may include data capture and recording devices. In some instance, the drone devices 170 may include one or more cameras, one or more motion sensors, one or more microphones, one or more biometric collection tools, one or more temperature sensors, one or more humidity sensors, one or more airflow sensors, and/or other types of sensors that may be useful in capturing monitoring data related to user safety. For example, once dispatched to a location where the user may require emergency assistance, the drone devices 170 may capture a video feed of the user showing the extent of injury and transmit the video feed to either the application server 180 or the emergency notification server 190 to alert emergency responders about the user's condition. In other examples, the drone devices 170 may be outfitted with thermal-imaging cameras capable of identifying locations, people, or pets through structural features of a location. For example, the drone devices 170 may be deployed to a property in which a user is located and may use the thermal-imaging cameras to determine a particular location within the property where the user may be trapped inside the property. In such examples, the drone devices 170 may transmit the captured thermal video footage to the emergency notification server 190 such as a nearby fire station.

In some implementations, the drone devices 170 may also include output devices. In such implementations, the drone devices 170 may include one or more displays, one or more speakers, one or more projectors, and/or any type of output devices that allow the drone devices 170 to communicate information to nearby emergency contacts. For example, if a user is physically disabled as the result of an incident and unable to use wearable devices 150 or mobile devices, the user may record a distress message or video using the drone devices 170, which may then transmit the message or video to the application server 180 or the emergency notification server 190.

In some implementations, the drone devices 170 may be configured to record visual verifications and/or identify perpetrator identification for particular types of incidents. For example, in response to safety incidents determined by the application server 180, the application server 180 may deploy the drone devices 170 to record video footage. In some instances, the drone devices 170 may be configured to operate within certain geographic regions (e.g., a gated residential community). The drone devices 170 may be centrally operated by a security provider such as an alarm security company providing security services to a particular geographic region. In such instances, the drone devices 170 may be stored in a central home base with a charging and control station and deployed as a mobile solution in response to an incident signals for users.

In some implementations, the drone devices 170 may be delivery drones (e.g., a parcelcopter) that may be utilized by the monitoring platform 100 to provide supplies or other equipment to a user in response to the application server 180 detecting the occurrence of an incident. For instance, the drone devices 170 that are delivery drones may be used to dispatch first aid kits and/or other emergency medical equipment (e.g., gauze, bandages, braces, epi pens, tourniquets, etc.). In such instances, the drone devices 170 may delivery particular supplies based on the classification of the incident by the application server 180.

In some implementations, after the application server 180 determines an incident, the application server 180 may select the particular drone device 170 to deploy to the incident from a set of drone devices 170 based on particular attributes such as, for e.g., charge levels, location of the incident, and the direction of user movement. For example, the set of drone devices 170 may include various drone devices 170 with varying battery capacities, aerial speeds, and/or device features. In such examples, the monitoring platform 100 may choose the particular drone device 170 to be deployed that can get to the location of the incident the fastest and has enough battery to monitor the user for a reasonable amount of time (e.g., fifteen minutes).

In some implementations, multiple drone devices from the set of drone devices 170 may be deployed based on the particular nature of the safety incident. For example, the application server 180 may deploy multiple drone devices if the received user data indicates the safety incident is a life-critical incident (e.g., a house fire) that causes a loss of life. In some instances, the multiple drone devices may be deployed sequentially to maximize response time and conserve resources. For example, the multiple drones may include a diagnostic drone device, which is deployed initially to minimize response time, and a support drone device that provide the user with emergency supplies to help with the emergency event. In another example, an initial drone device may be deployed to minimize response time while a secondary drone is deployed as a backup if the battery of the initial drone runs out.

The application server 180 may be an electronic device configured to determine a safety incident of a user. For example, the application server 180 may determine from received sensor data whether the user is injured or in danger. To make the determination, the application server 180 may provide control services by exchanging electronic communications with the monitoring control unit 110 and the one or more mobile devices 130, 140 over the network 105. For example, the application server 180 may be configured to monitor user data generated by the devices connected to the monitoring platform 100 such as the sensors 120, the one or more mobile devices 130, 140, the wearable devices 150, the one or more wireless sensor beacons 160, and the drone devices 170. In this example, the application server 180 may exchange electronic communications over the network 105 to send and/or receive information regarding user activity such as biometric data, activity data, location data and health data. The application server 180 also may receive information regarding activity within or external to the property from the one or more mobile devices 130, 140 or the wearable devices 150.

In some implementations, the application server 180 may store a user profile with user data transmitted from the devices connected to the monitoring platform 100 as represented in FIG. 2A. For instance, the devices connected to the monitoring platform 100 may periodically transmit various types of user data to the application server 180. The application server 180 may aggregate the different types of user data such as personal data, biometric data, activity data, and historical data into a user profile. In some instances, the application server 180 may use the user profile to learn normal usage patterns such as activity patterns (e.g., common exercise routines) and normal biometric measurements (e.g., resting heart rate, baseline blood pressure, normal skin temperature, baseline breathing rate). For example, the application server 180 may periodically receive user data collected by the devices connected to the monitoring platform 100 such as, for e.g., the one or more mobile devices 130, 140, or the wearable devices 150, and log the user data into the user profile. The application server 180 may then aggregate the received user data over particular time periods (e.g., six months) and perform trend analyses to determine normal biometric measurements for the user. In another example, the application server 180 may receive user activity data (e.g., steps taken, calories burnt) and compare the activity data with location data to determine usage patterns such as exercise locations, exercise routines, and other activity patterns.

In some implementations, the application server 180 may determine incidents and generate incident reports indicating that a user requires emergency assistance. For example, an incident may be any type of safety incident that is detected by the application server 180 based on the user data collected by the devices of the monitoring platform 100. For example, the application server 180 may determine that a user may be having a heart attack based on the particular wearable device 150 that measures heart rate data that the current heart rate is too high compared to a reference measurement. In response, the application server 180 may transmit an incident report to the emergency notification server 190 that includes various types of user data such as, for e.g., heart rate measurements, user activity data indicating prior physical activity, historical measurements of heart rates hours prior to the incident. In some instances, the incident report received by the emergency notification server 190 may include a control panel interface as represented in FIG. 2B.

In another example, the application server 180 may determine from received sensor data that a user was running along a trip route saved in a user's profile and mid-way between the route, the user's breathing pattern and heart rate corresponded to those when the user is unconscious or asleep and that the user is still moving. In response, the application server 180 may determine that there is a safety issue. For example, the application server 180 may determine that the user may have been kidnapped. If the application server's 180 confidence that the user has been kidnapped is high, the application server 180 may immediately notify emergency personnel. If the application server's 180 confidence that the user has been kidnapped is moderate, the application server 180 may display a prompt and an audio alert on the user's mobile device, wearable device or heads up display indicating that the application server 180 has determined that the user may be in danger and how the application server 180 made the determination, and a countdown indicating that emergency personnel will be notified if the user does not verify that there is no safety issue within a specific period of time (e,g. thirty seconds). The application server 180 may require that the user enter a passcode on the user's mobile device to verify that no notification should be made.

In some instances, the application server 180 may be configured to determine particular duress codes sent by the user in the event of an emergency incident. For instance, the user may enter a pre-determined or customized duress code it appears as if the user has cancelled the alarm but actually transmits a duress signal to the application server 180. For example, the user may enter the duress code during a robbery.

In yet another example, the application server 180 may receive an indication that a user has activated a panic button on a necklace worn by the user, sensor data indicating that the user was traveling at a high speed corresponding to a car and is no longer moving, and sensor data indicating that the user's car airbags have deployed. In response, the application server 180 may determine that the user has been in a car accident and is seriously injured and may notify emergency personnel accordingly.

In some instances, the application server 180 may monitor the user location of the user when he/she is close to or inside the property to determine how to process an incident signal. For example, if the user is involved in an incident outside the property, the application server 180 may transmit the incident signal to the emergency notification server 190 and if the user is involved in an incident inside the property, the application server 180 may instruct the monitoring control unit 110 to transmit the incident signal to the home security provider for the home.

The emergency notification server 190 may be an electronic device of an emergency service provider configured to exchange communications from the devices connected to the monitoring platform 100 such as the sensors 120, the one or more mobile devices 130, 140, the wearable devices 150, the one or more wireless sensor beacons 160, the drone devices 170, the monitoring control unit 110, or the application server 180. For instance, the emergency notification server 190 may be configured to receive incident reports from the application server 180 in response to the application server 180 detecting a safety incident where a user requires emergency assistance. In such instances, the emergency notification server 190 may be an electronic device configured to an emergency responder such as an emergency medial responder, a fire department, or a public safety access point.

In some implementations, the emergency notification server 190 may be a third party entity separate from the monitoring platform 100. For example, the emergency notification server 190 may be a central alarm station for a security service provider, a campus security server in a school or school/university police department, or security gateway for a particular residential neighborhood. For instance, the emergency notification server 190 may be registered to the monitoring platform 100 using a connection bridge such as an application (e.g., mobile application including user accounts), using a unique user identifier such as a username and password or a Quick Response (QR) to add the third party monitoring platform 100 to the user profile of the monitoring platform 100. In other instances, the emergency notification server 190 may be registered to users within a particular geographic location (e.g., a gated residential community) where users within the geographical location are registered to the emergency notification server 190 of the particular location.

In some implementations, the application server 180 may determine the occurrence of an incident based on comparing extrinsic data surrounding the user location and the user data collected by the devices connected to the monitoring platform 100. For instance, the application server 180 may monitor current weather, daylight level, air quality, and/or other external conditions to determine whether the user data indicates suspicious conditions. For example, if the current weather indicates a thunderstorm, then the application server 180 may determine that the user location indicating that the user is stationary outside may be suspicious, e.g., the user may have been struck by lightning or the user is being forced to stay stationary outside. In another example, if it is night time, the application server 180 may determine that the user is more likely to be performing night time activities, e.g., stargazing, walking, jogging as opposed to football or basketball, and determine whether there is likely to be a safety incident based on the types of night time activities in which the user might have been engaged. In yet another example, if it is night time but the user data indicates that the user is currently performing activities outside that are better suited for sunlight, e.g., football or basketball, the monitoring platform 100 may also determine that this may be suspicious. In another example, if the user medical history in the application server 180 indicates that the user may have asthma but that the user is located in an area with low air quality, the application server 180 may predict that the user may likely have an asthma attack or may determine that the user is likely suffering an asthma attack.

In some implementations, the application server 180 may aggregate user data collected by devices of multiple users that are all connected to the monitoring platform 100 to gather data surrounding mass casualty incidents. For example, if there is a large-scale emergency within a particular location (e.g., earthquake, terror attack, public evacuation, etc.), the application server 180 may determine the presence of such an emergency based on aggregating suspicious data from multiple devices within the particular location. The application server 180 may compare the aggregated data to other types of environmental data (e.g., seismic activity, electromagnetic pulses, or radiation) that are be collected from sensors located nearby or within the particular location where there may be abnormal activity.

In some implementations, the monitoring platform 100 may additionally or alternatively include various features. For example, the monitoring platform 100 may include a peer-to-peer location sharing feature that enables users to send location information collected from the one or more mobile devices 130, 140 or the wearable devices 150 to emergency contacts. In another example, the monitoring platform 100 may include a distress signal forwarding feature that enables a user to transmit a distress signal including user location information from either the one or more mobile devices 130, 140 or the wearable devices 150 to the emergency notification server 190, which may be associated with an emergency responder such as, for e.g., a fire station, an emergency medical services facility, or a police station. In another example, the monitoring platform 100 may include mobile applications that use the location data collected by the one or more mobile devices 130, 140 and the wearable devices 150 to determine the nearby authorities having jurisdiction (AHJ) or the public safety access points (PSAP) in case of an emergency incident within the user location.

The monitoring platform 100 as described within this disclosure may be adapted to function with a variety of wearable devices, communication devices, and networks with long-term extensibility. For example, new wearable devices and applications may be adapted to operate with the monitoring platform 100 by adapting the new wearable devices to run mobile applications that are capable of exchanging communications with the devices connected to the monitoring platform 100. In some instances, the monitoring platform 100 may include a mobile application ecosystem that includes customized mobile applications that are built for particular mobile devices, wearable devices, communication devices, safety sensors, drone devices, and wireless sensor beacons such that these devices may exchange communications over the network 105 with emergency responders. For instance, particular examples of wearables device may include a smart motorcycle helmet or a smart skiing helmet that can transmit speed and crash information to emergency medical responders, including the location on the helmet of the impact(s) and the number of impacts(s). In another instance, vehicles such as cars, motorcycles, and public transportation may include smart sensors that transmit distress signals to nearby emergency responders in response to a vehicular crash. In other instances, wearable devices may include miniaturized personal health devices used to monitor the movement of patients with chronic diseases such as, for e.g., Parkinson's disease.

FIGS. 2A-2C illustrate example user interfaces in a safety monitoring platform. FIG. 2A represents a user interface 200A including a user profile that collects various types of data. FIG. 2B represents a user interface 200B for viewing incident reports. FIG. 2C represents a user interface 200C that determines if a user requires emergency assistance.

Referring now to FIG. 2A, the user interface 200A may include a user profile 210 that displays general information 212, user data types 214, and user data 216. The user profile 210 may be associated with each user that is registered within the monitoring platform 100. For example, registered users may include users that use the devices connected to the monitoring platform (e.g., one or more mobile devices 130, 140, the wearable devices 150, etc.) or emergency contacts of such users. In some instances, a separate user profile 210 is created for each particular device connected to the monitoring platform 100. For example, the wearable devices 150 may associate a particular user profile 210 for each registered user and the one or more mobile devices 130, 140 may associate a different user profile 210 for each registered user.

The user profile 210 may include general information 212 as represented in FIG. 2A. In some instances, the general information 212 may also include email, phone number, and/or any other information that identifies the registered user. The user profile 210 may also include other data types 214, which represent the different types of user data generated by the monitoring platform 100. For example, the user profile 210 may include contact information for emergency contacts in an address book of family of friends with names, emails, phone numbers, or physical addresses that the monitoring platform 100 contacts in cases of emergency or when registered user requires assistance. In another example, the data types 214 may include biometric data such as height, weight, heart rate, blood pressure, blood type and breathing rate. In another example, the data types 214 may include activity data such as exercise routines, common walking or running routes, steps taken, and other types of exercise data. The data types 214 may also include historical data that includes previous user data within a particular time period (e.g. 6 months) and may be used by the monitoring platform 100 as reference data when comparing to current user data to determine the occurrence of an emergency incident. In some instances, the historical data may be transmitted to the user and/or other specified contacts during reoccurring time intervals (e.g., weekly).

In some implementations, the user profile 210 may include user selections identifying people or pets that the user of the user profile 210 frequently go on "trips" including rules that reference the people or pets that are a part of the "trip." A "trip" may represent any outdoor activity outside the user's home such as, for e.g., running exercises, work or school commutes, common or reoccurring travel paths, or frequent locations visited. In some instances, the user selections identifying the people include other registered users of the monitoring platform 100. In such instances, the user data of each particular user may be shared amongst the particular user profiles 210 of each individual user during a "trip." For example, if two users participate in the same running exercise, the user data collected from each of their wearable devices may be aggregated by the monitoring platform 100 for incident detection.

In some implementations, the user profile 210 may be created for domestic pets that are frequently taken on "trips." For example, a registered user may create a user profile 210 for a dog that is regularly walked. In some instances, the dog may also wear a wearable device that locates and identifies the dog and stores corresponding data in the user profile 210 of the dog. In such instances, the user profile 210 may be used to identify the dog in case of an emergency incident.

In some implementations, the "trips" included in the user profile 210 may specify various types of user activity data. For instance, the "trips" may include user-specified routes for reoccurring activities such as running, hiking, walking pets. In other instances, the "trips" may include nearby points of interest such as local parks or transportation stops that user may frequently visit. In such instances, the wearable devices 150 may use the points of interests to map out frequent pathways used by the users to generate an activity log. In other instances, the time spent at points of interest may be tracked to generate activity information about how much time the user typically spends at the points of interest. For example, the amount of time spent may be compared to particular activities to correlate activity type and time spent at points of interest.

In some implementations, the user activity data specified by "trips" may be combined to generate a set of "trip rules" that represent particular user activities. For example, a "trip rule" may include a set of parameters such as a user activity (e.g., walking the dog), a time period for performing the user activity (e.g., 20 minutes), and a route between points of interest (e.g., down two streets from the user's property). In some instances, the monitoring platform 100 may initiate a "trip rule" manually after a user specifies that they are about to perform a particular user activity. For example, a user may submit an input to one of the devices connected to the monitoring platform 100 specifying the various "trip rule" parameters, and in response the monitoring platform 100 may track user activity to ensure that the "trip rule" is maintained. In other instances, the monitoring platform 100 may initiate a "trip rule" automatically based on detecting user activity indicating a likelihood that the user may be performing the particular activity associated with the "trip rule." For example, if a user is leaving his house at the same time and day of the week when he/she usually walks his dog, the "trip rule" for dog walking may be automatically initiated based on the monitoring platform 100 comparing the current user activity with historical data of user activity. As described above, the trip rules may be used by an application server to determine when there is a safety incident. For example, the application server may determine from the trip rules that a user is on a trip and in response, may determine the safety incidents that may be applicable when the user is on a trip.

In some implementations, the user profile 210 may additionally include designated safe routes or areas that represent user-specified routes or locations where the user exhibits normal activity. For example, the designated safe locations may include commonly visited locations such as a user's home address, work address, or home addresses or frequent contacts. In other examples, designated safe routes may be routes that the user frequently follows between common locations such as a work commute, running routes, or other routes that indicate normal user activity.

Referring now to FIG. 2B, the user interface 200B may include a control panel interface 220 that displays data visualization tabs 222, a current status 223, a user location 224, milestones 225, and historical data 226. The control panel interface 220 may be a software application running on the application server 180 and designed for use by a central system operator of the monitoring platform 100. For example, the control panel interface 220 may be used to route incident signals transmitted from devices connected to the monitoring platform 100, for e.g., the one or more mobile devices 130, 140, the wearable devices 150, the one or more wireless beacons 160, or the drone devices 170, to the emergency notification server 190.

The control panel interface 220 may display data visualization tabs 222. For example, as shown in FIG. 2B, the data visualization tabs 222 may include "DASHBOARDS," "ANALYSIS," "REPORTS," and "CONFIG." The data visualization tabs 222 may alter the data displayed on the control panel interface 220. As shown in the example, the "DASHBOARDS" tab displays information related to an incident signal. In another example, the "REPORTS" tab displays user reports that include previously received user data from devices within a particular geographic location (e.g., a neighborhood community, or a postal zip code), or certain types of users (e.g., residential vs. commercial users). In such an example, the user reports may include locally cached user data on the application server 180. In another example, the "CONFIG." tab may include filters to adjust views of the received incident signals such as viewing by zip code, incident type, severity, or other classifications.

The control panel interface 220 may also display a current status 223. The current status 223 shows information related to a recently received incident signal. The current status 223 may include an incident description that represents a textual description of the particular type of incident, an incident classification that may represent a prediction of the type of incident by the monitoring platform 100, a current location for the particular device generating the incident signal, an incident duration describing the time lapse between when the incident signal has been transmitted, and an incident level that represents the severity of the incident signal.

As shown in the example, the incident signal may include an elevated heart rate (e.g., 100 beats per minute), which is indicative of a potential heart attack. In response, the monitoring platform 100 may provide an incident description that indicates that the user may need medical assistance. Based on the user data included in the incident signal, the monitoring platform 100 may determine that incident is seventy percent likely to be a heart attack. The monitoring platform 100 may also include alternative likelihoods based on additional user data nearby the user device transmitting the incident signal. For instance, if the incident signal is generated in a densely populated location with high traffic volumes, the monitoring platform may determine, based on such extrinsic data, that an alternative classification for the incident may be a pedestrian accident. In some instances, the control panel interface 220 may also display a list of leading factors based on the user data included in the incident signal.

The monitoring platform 100 may determine a current location of the incident based on location data included in the incident signal. As shown in the example, the monitoring platform 100 may also determine an average response time based on determining nearby emergency service stations such as finding nearby hospitals and fire stations as will discussed more specifically below. The monitoring platform 100 may use the predicted response time to generate a visualization that represents the urgency of the incident. In some instances, the current status 223 may also display an incident level that represents a severity prediction by the monitoring platform 100. For instance, the monitoring platform may calculate a multi-factorial score, e.g., between one and ten, that represents a user risk as a result of the incident. For example, if the user data included in an incident signal indicates minimal risk of harm or injury to the user, then the severity may be a lower number, for e.g., one, whereas if the incident is a heart attack that may cause death without emergency assistance, then the severity may be a higher number, for e.g., ten.

The control panel interface 220 may display a user location 224. The monitoring platform 100 may use global positioning system (GPS) data received from the user device transmitting the incident signal to determine the user position. The user location 224 may display a map with a pin to locate the user. As shown in the example, the map also includes points of interest such as, for e.g., landmarks and nearby emergency services. The user location 224 may also include a list of landmarks and nearby emergency services in relation to the user location and the current distance between the user position and the points of interest. The user location 224 may also display an option to select one of the points of interest displayed on the user location 224.

As shown in the example, an operator may select one of the nearby emergency notification servers from the list points of interest and press a button to notify local emergency notification servers and in response, the incident signal may be routed to the selected emergency notification server, which may be, for e.g., the emergency notification server 190. In some instances, the emergency notification server 190 may receive an incident report that includes user data identifying the user needing emergency assistance, location data of the incident, or relevant data related to the type of incident such as biometric data indicating a particular health-related injury (e.g., blood type, known allergens, medical history, recent heart rhythm that could indicate a potential heart attack).

The control panel interface 220 may display milestones 225. The milestones 225 may indicate events related to the incident such as, for e.g., when the incident signal transmitted from the user device, the incident signal being processed by the application server 180, or additional incident signals being transmitted representing user updates or conditions. For instance, if a particular incident is urgent, then the milestones 225 may indicate where in the transmission cycle the incident signal is currently in. In other instances, the milestones 225 may indicate potential signal transmission issues. For example, if the user device is destroyed in the incident, than the milestones 225 may indicate that alternative communication means, for e.g., communicating with an emergency contact, may be necessary.

The control panel interface 220 may display historical data 226. The historical data 226 may display user data over particular periods of time (e.g., six hours) that may indicate potential or insights related to the cause of the incident. As shown in the example, the historical data 226 may display measured heart rate over the last ten hours after the monitoring platform determines, based on the user data included in the incident signal, that the incident may be a heart attack. In such an example, the historical data 226 may show the measured heart rate relative to the baseline heart rate to represent problematic trends indicating the cause of the incident. In some instances, the data displayed in the historical data 226 may be transmitted to the emergency notification server to provide additional information about the incident to help emergency service responders provide assistance to the user. As shown in the example, if the incident is identified by the monitoring platform 100 as a user having a heart attack, heart rate data from hours before the incident may be transmitted in the incident report such that emergency medication technicians that are dispatched may have greater knowledge in assessing the user's physical condition.

Referring now to FIG. 2C, the user interface 200C may be shown on a mobile device 230, a wearable device 240, or a heads up display (HUD) (not shown) that display an incident notification 232, user response options 234, 236 and an automated response option 238. The mobile device 230 may be shown on devices connected to the monitoring platform 100 such as, for e.g., the one or more mobile devices 130, 140, or the wearable devices 150. The mobile device 230 may be presented to a user that is currently either wearing or carrying the device in response to the monitoring platform 100 determining that the user may need emergency assistance. A user may provide an input using either of the user response options 234, 236 indicating whether the alert is a false alarm or if the user does actually require medical assistance.

As shown in the example, the monitoring platform 100 may receive heart rate data from a particular wearable device 150, which regularly monitors the heart rate of a user. In response to detecting an abnormally high heart rate, for e.g., 100 BPM, the monitoring platform 100 may transmit the notification 232 to a particular device connected to the monitoring platform 100, for e.g., the one or more mobile devices 130, 140, or the wearable devices 150, asking the user if he/she needs medical assistance. The notification 232 may be transmitted to the particular user device electronically and may be presented either as an alert in the operating system of the particular wearable device 150, or through a mobile application that is installed on the particular user device, or shown on the HUD. In some instances, the heads up display may also be used to represent information related to the notification 232 using a virtual or augmented reality projection within the field of view of the user.

The user response options 234, 236 allow the user provide to provide a user input in response to the notification 232 indicating whether the incident trigger is a false alarm or if the user does actually need emergency assistance. As shown in the example, the user may provide an input on the user response option 234 if he/she does need emergency assistance, or user input response option 236 if he/she does not need emergency assistance.

In some instances, the user response options 234, 236 may additionally or alternatively include a code entry 242 that is displayed on the wearable device 240 for the user to submit a code that indicates whether the incident trigger is a false positive or a false negative. For example, in response to an incident trigger, the user may be presented with user response options 234, 236 that includes a code entry. The user may enter various codes corresponding to different user statuses such as, for example, a distress code that indicates that the user is in danger, a duress code that indicates that the user has cancelled the incident signal but is still in danger, or a cancel code that indicates that the incident trigger is a false positive signal.

In some implementations, the mobile device 230 may also include an automated response option 238 that shows a time period for providing a user input before emergency notification servers are automatically notified about the potential incident. For example, in some instances where a user is unable to provide an input to the one or more mobile devices 130, 140 or the particular wearable device 150 because of physical injury, the mobile device 230 may transmit an automated signal to the application server 180 indicating that the user has failed to provide a user input and an instruction that emergency notification servers should be dispatched to the user's location. In some instances, once the automated signal has been transmitted to the application server 180, the application server 180 may transmit an incident signal to the emergency notification server 190. Additionally or alternatively, the application server 180 may notify emergency contacts of the user that the user has failed to provide a response to a potential emergency incident.

In some implementations, notification 232 and the user response options 234, 236 may additionally or alternatively include incident-specific questions that are directed to gather information about user risk in response to the application server 180 potentially flagging an incident. For example, for abnormal heart rate measurements, the notification 232 may also include questions to the user such as, for example, "when was the last time you exercised?", or "when was the last time you felt a shortness of breath?", "do you have chest pain?", "are you light headed?", or "are you experiencing numbness, pain or tingling in your arms?". The user response options 234, 236 may include different response options such as time periods or gradations of severity. In such implementations, mobile device 230 may be utilized to gather user input during particular activities that are specifically likely to put a user in danger or may likely cause injury (e.g., an intense sporting event) and generating historical data that may be used to improve the predictive capabilities of the monitoring platform 100.

In some implementations, the notification 232 may be additionally or alternatively transmitted to the particular wearable device using other types of notification that alert a user such as, for e.g., an alert sound, a vibration, or other types of haptic feedback. In other implementations, the user response options 234, 236 may include other types of user input such as, for e.g., providing a unique password or passphrase, a unique gesture, or a voice query.

In some implementations, the notification 232 may be transmitted redundantly to multiple users that are registered to the monitoring platform 100. For example, in some instances, the notification 232 may be transmitted to both the user and an emergency contact to notify the emergency contact that the user may potentially need emergency assistance. As discussed previously in FIG. 2A, in other examples where a particular is associated with a "trip," the monitoring platform 100 may transmit the notification 232 to all user that are designated as being associated with the "trip" if the incident falls within the boundaries set by the "trip" (e.g., particular location, particular time of day, particular user activity, etc.). Additionally or alternatively, in some instances, the user may specify notification settings that control how the notifications are transmitted to multiple users. In one example, a user may set the notification settings to indicate that the notification 232 may only be sent to contacts that are designated as emergency contacts in the user profile 210.

In other implementations, the notification 232 may be transmitted redundantly to multiple user devices connected to the monitoring platform 100. For instance, the notification 232 may be sent to both of the mobile device 230, the wearable device 240, and/or the HUD. In such instances, when one of the user devices is destroyed during an incident (e.g., a car crash), the notification 232 is transmitted to a working device to increase the likelihood of receiving a user input indicating whether a user needs medical assistance.

Figure 3A:
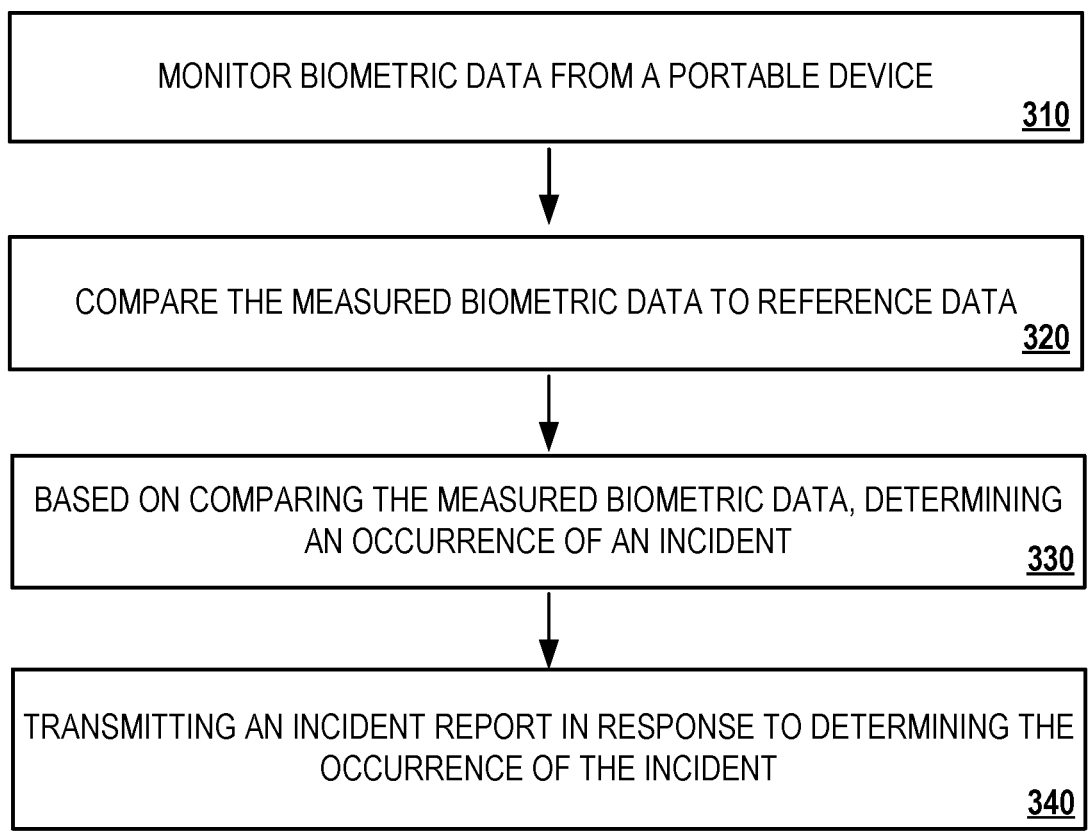
FIGS. 3A-3C illustrate examples of processes for detecting safety incidents.
Figure 3B:
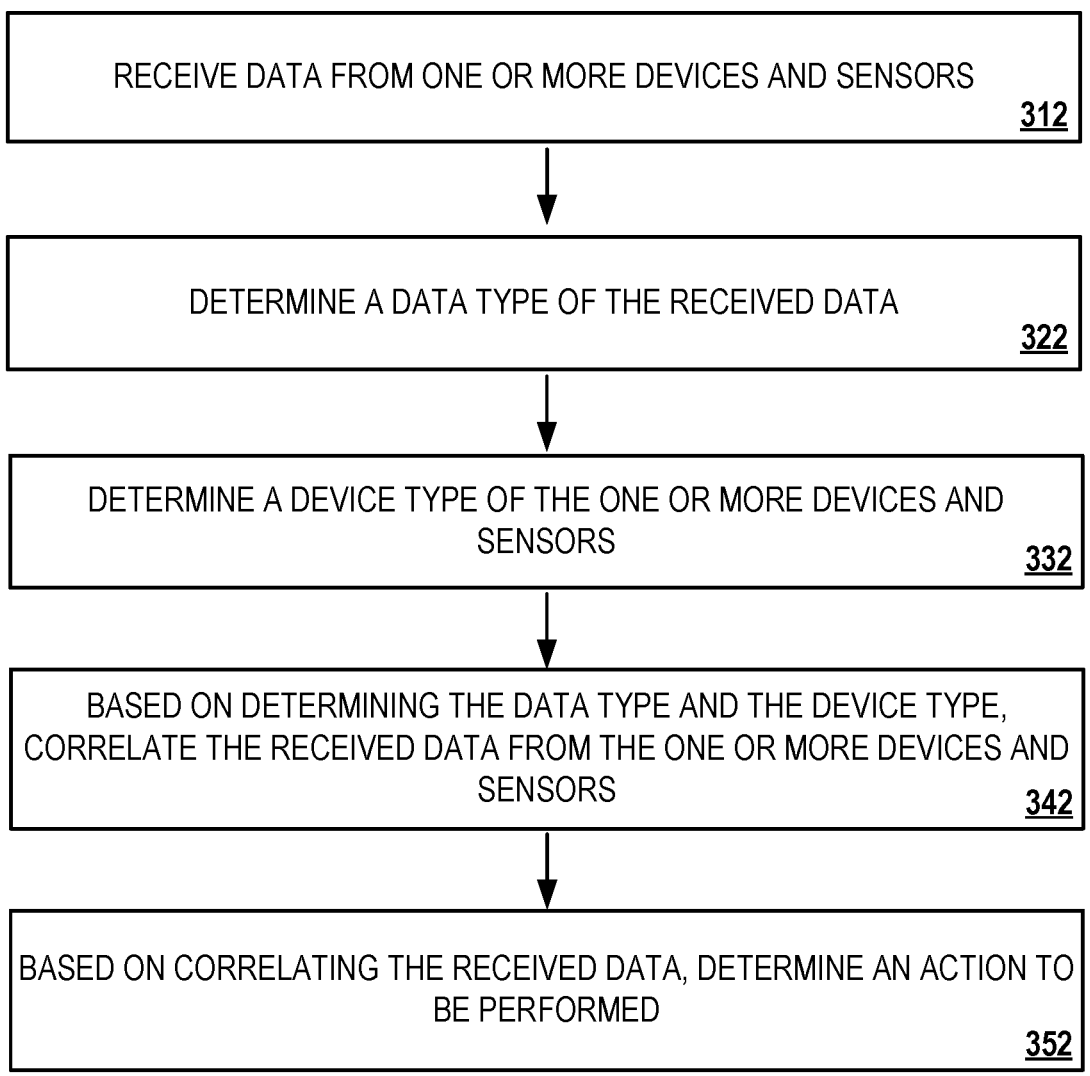
Figure 3C:
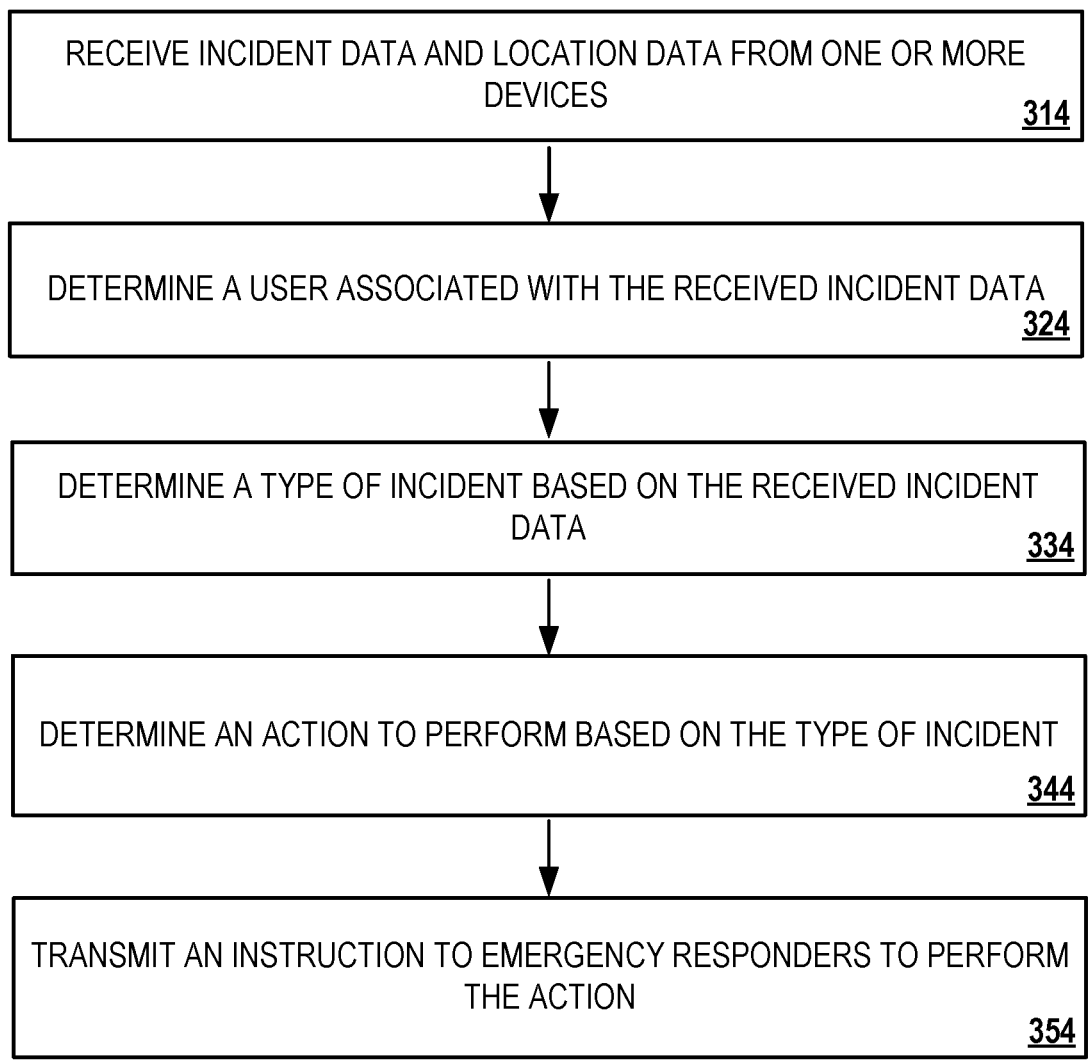

FIGS. 3A-3C illustrate example processes 300A-300C, respectively, for detecting user safety incidents outside a property. Briefly, the process 300A represents a process for determining the occurrence of an incident based on biometric data, the process 300B represents a process for determining an action to be performed in response to an incident based on data type and user type, and the process 300C represents a process for transmitting a signal to emergency responders in response to an incident.

Referring to FIG. 3A, the process 300A may include monitoring biometric data from a portable device (310), comparing the received biometric data to reference data (320), based on comparing the received biometric data, determining occurrence of an incident (330), and transmitting an incident report in response to determining occurrence of the incident (340).

The process 300A may include monitoring biometric data from a portable device (310). For example, the application server 180 may monitor biometric data measured by devices connected to the monitoring platform 100 such as, for e.g., the one or more mobile devices 130, 140 or the wearable devices 150. For instance, biometric data may include heart rate, heart rhythm, skin temperature and moisture, breathing rate, blood pressure, and any other health-related user data. The application server 180 may collect the biometric data periodically over particular periods of time (e.g., daily, weekly, etc.) and store it within a repository on the application server 180.

The process 300A may include comparing the measured biometric data to reference data (320). For example, the application server 180 may compare the measured biometric data from the particular wearable device 150 against reference data stored on the application server 180. The reference data may be historical data collected previously from the user to establish a baseline measurement (e.g., baseline heart rate, baseline blood pressure, etc.). For example, the reference data may be initially measured when the user creates the user profile 210 within the application server 180 or sets up the particular wearable device 150 as a new device connected to the monitoring platform 100.

In some instances, the reference data may be updated as the application server 180 collects historical user data that suggests general trends that baseline measurements have changed. For example, if a user begins a new exercise routine that impacts his/her baseline heart rate over six months, the application server 180 may adjust the reference data including baseline heart rate based on determining that the historical heart rate data over six months indicates an increase in baseline measurements. In such implementations, the application server 180 may aggregate historical data and perform linear regression analysis to determine whether the changes in baseline measurements are indicative of physiological changes or due to external conditions (e.g., seasonal weather changes, changes in environment, etc.).

In some implementations, the application server 180 may also aggregate biometric data from other users within a particular group or classification (e.g., gender, age group, geographic location, etc.) to calculate the reference data to compare the measured biometric data. In such implementations, the reference data may include historical biometric data from other users that are identified by the application server 180 as being similar to the user of the measured biometric data. For example, the application server 180 may aggregate heart rate data based on gender, age demographic, for a particular activity such as running to determine reference biometric data for a particular user performing such an activity.

The process 300A may include, based on comparing the measured biometric data, determining an occurrence of an incident (330). For example, the application server 180 may determine the occurrence of an incidence in response to determining that the measured biometric data is abnormally high or abnormally low compared to the reference data. In such implementations, the application server 180 may use a threshold level of difference between the measured biometric data and the reference biometric data. For example, the application server 180 may determine that a user is having an incident such as a heart attack when a user's measured heart rate is 100 beats per minute (BPM) compared to the user's baseline heart rate of 63 BPM. In such an example, the threshold level of difference between the measured heart rate and the baseline heart rate may be 30 BPM. Other examples of data that the application server 180 may compare irregular heart rhythms, increased sweating, exhaustion, pain indications in arms, neck, or shoulders. In such examples, the application server 180 may send periodic instructions to the mobile device 130 or the wearable device 150 to collect information from the user.

In other instances, received user data may also indicate an occurrence of an incident. For example, a sudden acceleration or deceleration of biometric data (e.g., heart rate, breathing rate, blood pressure, skin temperature, skin moisture). In other instances, an abnormal location relative to an expected route or a designated safe area, an unusually slower or faster user pace, a particular gyroscopic position (e.g., closer to the ground), sounds associated with distress detected by a microphone, or the user not returning to an expected location with a particular time period (e.g., not unlocking a door with their unique user code or disarming a security system within a specified time period), may also indicate the occurrence of an incident.

In some implementations, the application server 180 may alternatively determine the occurrence of an incident without comparing the measured biometric data to reference data. For instance, in such implementations, instead of comparing the measured biometric data to reference data, the application server 180 may instead track the measured values over a particular period of time to determine the occurrence of an incident. For example, the application server 180 may track heart rate measurements from either the mobile device 130 or the wearable device 150, and in response to detecting an acute decrease or increase in measured heart rate, determine an occurrence of an incident that may be a heart attack. In such an example, the application server 180 determines the occurrence of the heart attack incident without comparing the reference measured heart rate data to reference heart rate data.

The process 300A may include transmitting an incident report in response to determining occurrence of the incident (340). For example, the application server 180 may transmit the incident report to the emergency notification server 190. In some implementations, as represented in FIG. 2B, the application server 180 may include a control panel interface 220 for displaying generated incident reports from the devices connected to the monitoring platform 100. In some instances, the application server 180 may also send incident reports to emergency contacts identified in the user profile 210 associated with the user involved in the incident. In such instances, the incident report may include relevant user data and a notification indicating that the user may need emergency assistance.

Referring now to FIG. 3B, the process 300B may include receiving data from one or more devices and sensors (312), determining a data type of the received data (322), determining a device type of the one or more devices and sensors (332), based on determining the data type and the device type, correlate the received data from the one or more devices and sensors (342), and based on correlating the received data, determining an action to be performed (352).

The process 300B may include receiving data from one or more devices and sensors (312). For example, the application server 180 may receive user data from devices connected to the monitoring platform 100 such as, for e.g., the sensors 120, the one or more mobile devices 130, 140, or the wearable devices 150.

In some implementations, in addition to receiving user data from devices connected to the monitoring platform 100, the application server 180 may also receive extrinsic data surrounding the user location and the user data collected by the devices connected to the monitoring platform 100. For instance, the application server 180 may receive data indicating the current weather, daylight level, air quality, and/or other external conditions to determine whether the user data indicates suspicious conditions.

The process 300B may include determining a data type of the received data (322). For example, the application server 180 may categorize various types of user data such as, for e.g., biometric data, activity data, location data, or scheduling data. The application server 180 may include a repository of data types that include keywords, data values, and data categories that are associated with particular data types. For example, user data including heart rate may be categorized as biometric data whereas steps walked may be categorized as activity data.

The process 300B may include determining a device type of the one or more devices and sensors (332). For example, the application server 180 may categorize the devices connected to the monitoring platform 100 that generate and transmit the user data. For instance, the application server 180 may determine the type of mobile device of the one or more mobile devices (e.g., the operating system), the type of device of the wearable devices 150 (e.g., fitness tracker, smartwatch, audio recorder, heart rate monitor, etc.), or the type of sensor of the one or more sensors 120 (e.g., motion sensor, temperature sensor, occupancy sensor, etc.). In some instances, the application server 180 may also determine the manufacturer and serial number of the devices and include this is the device type.

The process 300B may include, based on determining the data type and the device type, correlating the received data from the one or more devices and sensors (342). For example, the application server 180 may correlate data transmitted by particular device types that are complementary and may allow the monitoring platform to generate predictions of user activity and conditions. For instance, heart rate data from a wearable device 150 may be correlated with weather data from the one or more mobile devices 130, 140 to determine if the outside weather conditions may place the user at risk of dehydration or excessive fatigue based on the temperature and humidity in the location where the user may be located. In another example, location data transmitted from the one or more mobile devices 130, 140 may be correlated with activity data transmitted from the wearable devices 150 to determine common exercise patterns (e.g., time periods of activity, reoccurring exercise locations, frequency of exercise, etc.). In such implementations, the correlated data may be aggregated into a data model that predicts current user conditions and calculates a likelihood of the user getting involved in a safety incident.

The process 300B may include, based on correlating the received data, determining an action to be performed (352). For example, the application server 180 may determine an action to be performed based on correlating the received user data from devices connected to the application server 180. For instance, the application server 180 may initially predict a potential based on the correlated data, and in response, determine an action that addresses the incident to ensure user safety.

For example, after correlating heart rate data indicating an elevated heart rate with location data indicating that the user is stationary and activity data indicating that the user was currently performing running exercises, the application server 180 may initially determine that the user may be at risk of a heart attack. The monitoring platform 100 may then determine that the action to be performed may be to transmit a distress signal to emergency medical responders with the user location and biometric data indicating symptoms of a heart attack. In another example, after correlating current location data with activity data indicating an expected route and heart rate data, the application server 180 may determine that the user may have been kidnapped based on determining that the user is moving faster than expected in a different route than expected and has an elevated heart rate. The application server 180 may then determine that the action to be performed may be to contact law enforcement authorities with a signal indicating that a kidnapping may have taken place.

In some implementations, the action to be performed may include providing notifications to emergency contacts. For example, the application server 180 may provide notifications that include performing an action (e.g., sounding a siren, generating alert beeps, or flashing a light indicator) in the home security system of the user's property or at the home security system of an emergency contact's property. In another example, the application server 180 may provide an alert to user devices of emergency contacts either through email, SMS, a mobile application, or other communication standards. In some instances, particular emergency contacts may be contacted based on their proximity to the incident location. For example, the application server 180 may provide notifications to individuals that are located within a particular radius (e.g., five miles) of the potential incident and are identified as emergency contacts. In other examples where the incident may take place on commercial or university property, the action to be performed may include alerting local authorities such as security personnel, campus police, or other private emergency response personnel.

In some implementations, the action to be performed may include enabling local privately or publicly-owned cameras to capture video feeds of the incident as it is taking place. For example, in such implementations, the application server 180 may determine the incident location based on location data included in the received user data and then camera feeds that may be accessible near the incident location.

In other implementations, the action to be performed may include deploying one or more drones to the user location to capture live video footage of the user and transmit the live video footage of the user to emergency responders to improve the chances of recovery.

Referring now to FIG. 3C, the process 300C may include receiving incident data and location data from one or more devices (314), determining a user associated with the received incident data (324), determining a type of incident based on the received incident data (334), determining an action to be performed based on the type of incident (344), and transmitting an instruction to emergency responders to perform the action (354).

The process 300C may include receiving incident data and location data from one or more devices (314). For example, the application server 180 may receive an incident signal including location data transmitted using devices connected to the monitoring platform 100 such as, for example, the one or more mobile devices 130, 140, or the wearable devices 150. In some instances, the incident signal may be manually transmitted by the user after an incident takes place and the user needs emergency assistance. In other instances, the incident signal may be automatically transmitted by the devices connected to the monitoring platform 100 in response to measuring user data that indicates an abnormality compared to expected levels for user data. For example, if a user loses consciousness during an exercise routine and remains stationary, the wearable device 150 may determine, based on the reduced breathing pattern and user motion, that the user may need medical assistance and automatically transmit an incident signal to the application server 180.

The process 300C may include determining a user associated with the received incident data (324). For example, the application server 180 may parse user profiles to identify the user associated with the received incident data. In some instances, the user profile may be associated with the received incident data using a unique user identification number that is included in the received incident data. In other instances, the device generating the incident data such as, for e.g., the one or more mobile devices 130, 140 or the wearable devices 150 may be associated with user profiles stored on the application server 180.

The process 300C may include determining a type of incident based on the received incident data (334). For example, the application server 180 may parse the received incident data to determine the type of incident that the user may be experiencing. For instance, the incident data may include a distress signal message from the user indicating the particular problem that the user may be experiencing. In such instances, the application server 180 may parse the distress signal message for particular keywords to classify the type of incident. For example, if the distress signal message includes health-oriented keywords such as "pain," "heart," "breathing," the application server 180 may classify the incident as a health risk, whereas if the distress signal message includes safety-related keywords such as "help," "secure," or "robbed" the monitoring platform 100 may classify the incident as a safety or security risk.

In other implementations, the incident data may include all current user data measured by the devices connected to the monitoring platform 100. In such implementations, the application server 180 may correlate and aggregate the user data to classify the incident based on the most likely classification of the event. For instance, if the incident data includes elevate heart rate and increased breathing rate, the application server 180 may classify the incident as a health-related incident, whereas if the incident data includes unusual location data and/or activity data that suggests irregular or abnormal activity, the application server 180 may classify the incident as a safety-related incident.

The process 300C may include determining an action to be performed based on the type of incident (344). For example, after classifying the type of incident that the user may be experiencing, the application server 180 may determine an appropriate action that needs to be performed to reduce risk of injury from the incident. For instance, if the incident is classified as a health-related incident, the application server 180 may then aggregate the received biometric data to determine a predicted treatment to reduce the risk of physical injury. For example, if the heart rate data indicates that the user may be experiencing a heart attack, the application server 180 may determine that the action to be performed may be to provide oxygen therapy or other actions for the treatment of chest pain.

The process 300C may include transmitting an instruction to emergency responders to perform the action (354). For example, after the application server 180 has determined an action to be performed in response to the classified incident, the application server 180 may then transmit an instruction to the emergency notification server 190 to perform the action. For instance, the emergency notification server 190 may be an emergency room department of a hospital, a police station, a fire station or any other type of emergency responder. In such instances, the instruction may include relevant user data, a description of the problem, and a potential recommendation based on the user data received from the devices connected to the monitoring platform 100. For example, if the application server 180 determines that the user is at risk of a heart attack, the instruction to the emergency notification server 190 may include heart rate data, breathing data, blood pressure data, and medical history of the patient from the user profile. The instruction may also include a recommended treatment option based on common emergency treatments for heart attacks. In another example, if the application server 180 determines that the user is in a house with a fire, the instruction may include temperature data, information about the property from the user profile and recommendations for potential entrances and exits to the location where the user is trapped.

In some implementations, the instruction to the emergency responders may be transmitted by an operator that receives the incident signal through an interface on the application server 180. In such implementations, the operator may connect to an emergency responder such as, for e.g., a 911 operator or PSAP, using the control panel interface 220 as represented in FIG. 2B. For example, the operator may transmit live and recorded video footage captured by deployed drone devices 170, establish an audio bridge between the user device (e.g., the one or more mobile devices 130, 140 or the wearable devices 150) and the emergency responder, or request information from nearby emergency contacts or neighbors to gather information about the incident.

Figure 4:
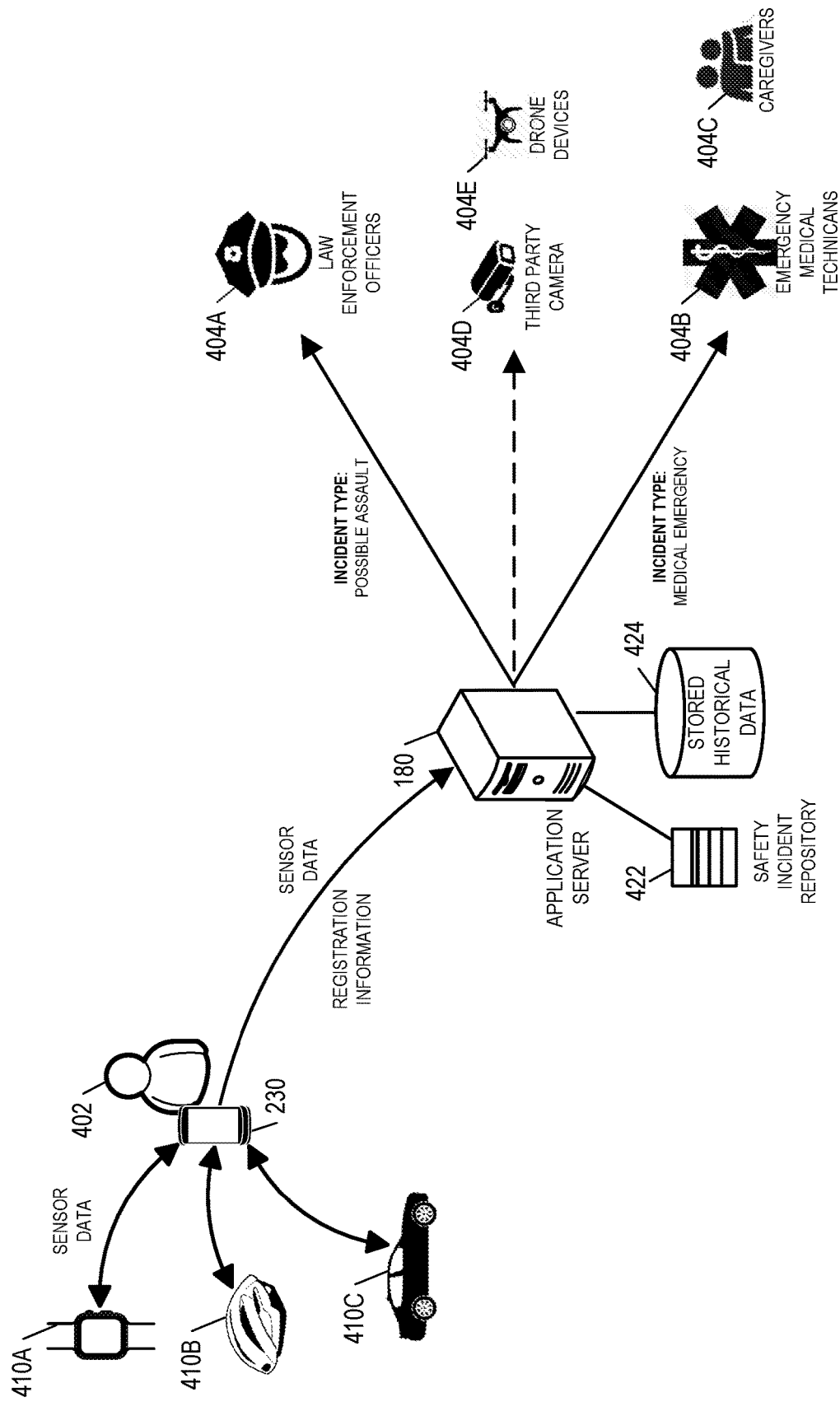
FIG. 4 illustrates examples of transmission sequences for a detected occurrence of a particular type of safety incident experienced by a user.

FIG. 4 illustrates examples of transmission sequences for detected occurrence of safety incidents experienced by a user 402. The occurrence of a safety incident may initially be determined by the application server 180 based on sensor data obtained from various safety devices 410A, 410B, and 410C. The application server 180 then identifies a classification for the particular safety incident experienced by the user 402, and then transmits a communication indicating the occurrence of the particular safety incident to another user or entity based on identified classification.

The safety devices 410A-C may be different types of sensing devices (e.g., a wearable smart watch, a helmet with an integrated impact sensor, a vehicle operated by the user 402) that collect different types of sensor data that indicate present safety conditions associated with the user 402. For instance, as discussed above, the safety device 410A may collect various biometric measurements that indicate a present physical condition of the user 402. As an example, the safety device 410A may be a wearable device that periodically measures the heart rate or the breathing rate of the user. In this example, if the measured rate exceeds or drops below a predetermined threshold associated with the baseline heart rate of the user 102, then this information may be used by the application server 180 to identify the occurrence of a safety incident experienced by the user 402.

In another instance, the safety device 410B may be a wearable device that includes impact detection sensors that are configured to detect when the user 402 has been involved in a possible accident collision and requires immediate medical assistance. As an example, the safety device 410B may be a bicycle helmet worn by the user 402 that detects when the user 402 has possibly fallen off his/her bicycle and may be injured but is unable to request medical assistance because he/she is unconscious. In this example, the safety device 410B may include an aftermarket sensor device that is placed on a surface of the helmet. The aftermarket device may include one or more gyroscopes and/or accelerometers that enables the detection of a crash event when the user 402 rides a bicycle by performing various types of inertial measurements.

In another instance, the safety device 410C may be a vehicle (e.g., a bicycle or car) that includes sensors that collects information on the user's operation of the vehicle. For example, a car may include a sensor that tracks vehicle movements (e.g., number of directional changes, vehicle speed, frequency of hard breaking, etc.) that are indicative of vehicular accidents and/or other safety incidents. In this example, the data collected by sensors can be used to determine if the user 402 has been involved in an accident and may be unconscious or unable to request emergency assistance.

Additionally or alternatively, the safety devices 410A-410C may provide some information that other safety devices also provide. For example, a safety device in the form of a smartwatch worn on a wrist may provide a geographic location corresponding to a user along with other biometric specific information and a safety device in the form of a vehicle may also provide a geographic location corresponding to a user along with other vehicle movement information.

In some implementations, the sensor data collected by each of the safety devices 410A-C may be directly transmitted to the application server 180. In such implementations, the application server 180 may receive registration information for the user 402 that identifies the safety devices that are registered to the user 402. The registration information may be included in a user profile stored within the stored historical data 424 as discussed above. The registration information may also include device identifiers that enable the application server 180 to associate incoming data transmissions from the safety devices 410A-C with the user profile of the user 402.

Additionally or alternatively, the safety devices 402 may also transmit sensor data to the client device 230 associated with the user 402. In such implementations, the safety devices 410A-C may be configured to exchange communications with the mobile device 230 using one or more wireless communication protocols (e.g., Bluetooth, near-field communication, etc.). The mobile device 230 may then be used as an intermediate device that processes the received sensor data from the safety devices 410A-C, aggregates the sensor data into a single data package, and transmit the aggregated data package to the application server 180 through a cellular data connection.

In some implementations, the mobile device 230 may label the sensor data provided to the application server 180 with an identifier for the user 402 so that the application server 180 may determine that the received sensor data is for the user 402. The mobile device 230 may determine to provide the information from a particular safety device in response to determining that the user 402 has registered the safety device as a device that the user 402 would like for the mobile device 230 to provide the application server 180 for safety monitoring purposes.

Additionally or alternatively, in some implementations, the safety devices 410A-C may be configured to redundantly exchange data communications with the application server 180 to minimize latency in data transmissions from the safety devices 410A-C that indicate a life-threatening emergency condition for the user 402. For instance, in such implementations, the safety devices 410A-C may be configured to identify a severity associated with an occurrence of a safety incident experienced by the user 402, and adjust the transmission of data accordingly to maximize the likelihood of sensor data being received by the application server 180. As an example, if the user 402 has been involved in a collision that destroys the mobile device 230 and makes the user 402 unconscious, then the safety devices 410A-C may redirect the transmission of sensor data directly to the application server 180 instead of through the mobile device 230. In another example, sensor data that is determined to include life-critical information (e.g., data indicating a vehicle fire) may be redundantly transmitted over multiple transmission pathways to maximize the likelihood that life-critical information is received by the application server 180.

Upon receiving the sensor data collected by the safety devices 410A-C and/or the registration information of the user 402, the application server 180 may determine whether the user 402 has experienced the occurrence of a safety incident. As described above, this determination may be based on a satisfaction of at least one condition associated with various types of safety indicators indicated by the sensor data. For instance, if the sensor data represents a monitored heart rate of the user 402, then an example of a safety indicator may be a threshold measured heart rate that is used to indicate that the user 402 is either experiencing anxiety and/or distress. In this example, sensor data indicating an abnormal high measured heart rate may be used to determine an occurrence of a safety incident associated with a medical emergency. In another instance, if the sensor data represents impact detection data, an example of a safety indicator may be a threshold measured acceleration towards the ground indicative of a crash or collision. In this example, accelerometer data indicating an abnormally high rate of motion towards the ground may be used to determine that the user 402 was involved in a crash while riding a bicycle.

The application server 180 may also determine a type of safety incident that is being experienced by the user 402. For instance, in some implementations, the application server 180 may access a safety incident repository 422 that specifies a list of different incident types (e.g., medical emergencies, personal attack by a perpetrator, traffic-related accidents, etc.), and select a particular incident type that coincides with the safety incident experienced by the user 402. The safety incident repository 422 may include mappings between incident type, related sensor data, and users/entities that can provide emergency assistance in response to the user. For example, the safety incident repository 422 may specify safety indicators for each incident type that are used to determine an occurrence of a particular type of safety incident.

In some implementations, determinations of the occurrence of safety incident and/or the particular type of safety incident by the application server 180 may be based on information included within the stored historical data 424. As described above with respect to FIG. 1, the stored historical data 424 may include historical information associated with the user 402, and/or historical information associated with other users that are determined to be similar to the user 402. For example, the application server 180 may obtain historical data that indicates user-specific information to identify the occurrence of related types of safety incidents (e.g., an increased likelihood of an occurrence of a heart attack if the historical data indicates a medical history of high blood pressure). In another example, the application server 180 may obtain public safety data for the location associated with the user 402 that indicates types of safety incidents experienced by other users (e.g., an increased likelihood of an assault in a high-risk location where other individuals have been reported to be attacked or an area of highway where other users have also been in car accidents).

Although the determination of the occurrence of the safety incident and/or the particular type of safety incident may be passively determined by the application server 180, in some implementations, such determinations may also be performed directly by the user 402. For example, the user 402 may submit one or more user inputs on the mobile device 230 indicating that he/she has recently experienced or is currently experiencing a safety incident. In such an example, the application server 180 may simply route the incident signal provided by the user 402 to the appropriate entity or user using similar techniques described throughout.

The application server 180 then generates and transmits a communication to notify the occurrence of the safety incident to another user. As described above, the generated communication may include information related to the obtained sensor data collected by the safety devices 410A-C. The communication may be selectively transmitted to a particular user/entity based on the occurrence of a particular type of safety incident determined by the application server 180 to be experienced by the user 402.

In the examples depicted in FIG. 4, if the application server 180 determines that the incident type for an occurrence of a safety incident is a potential assault, the application server 180 may transmit the generated communication to devices associated with a law enforcement officer 404A, e.g., servers of a law enforcement agency or a mobile computing device of a particular law enforcement officer. Alternatively, if the incident type is determined to be a medical emergency, the application server 180 may instead transmit the generated communication to devices associated with an emergency medical technician 404B or an authorized caretaker 404C.

In some implementations, the application server 180 may also transmit data related to the safety incident experienced by the user 402 to devices associated with external monitoring systems. As an example, if the system determines a safety incident has occurred in a particular location, then the application server 180 may transmit instructions to a third party camera 404D or a drone device 404E. In some instances, the third party camera 404D and the drone device 404E may be devices that are determined by the application server 180 to be nearby the occurrence of the safety incident experienced by the user. Accordingly, the third party camera 404D may pan and tilt to put the particular in view and provide the footage to the application server 180 to provide to safety responders. For example, the application server 180 may provide the footage to emergency responders 404B so that the responders have more context regarding the safety incident. In another example, the application server 180 may provide an instruction to the drone device 404E to fly to the particular location and similarly obtain video footage to provide others, or bring supplies for use in handling the safety incident. In some instances, the third party camera 404D and the drone devices 404E may be associated with a security service provided by a third party monitoring service provider 402. In such instances, the user 402 may have a subscription for monitoring and/or security services from the monitoring service provider.

In some implementations, the selective transmission of the communication may also include determining an appropriate user or entity based on the location of the user 402. For example, the application server 180 may receive location data from the mobile device 230 indicating a location associated with the occurrence of the safety incident experienced by the user 402. The application server 180 may determine that the user 402 is experiencing a medical emergency based on using techniques described above and identify an emergency medical technician as the entity to receive the communication. The application server 180 may then transmit the communication to the emergency medical technicians that are determined to be closest to the location associated with the occurrence of safety incident. In another example, the application server 180 may determine that the user 402 may be under duress and that the user 402 is on property of a particular entity and, in response, notify security associated with the entity and a law enforcement agency.

In some implementations, the application server 180 may also provide indications of areas that frequently have safety issues. For example, the application server 180 may include an indication in the communication to another user that the location the user is now in has had frequent assaults. In another example, the application server 180 may generate a report that indicates portions of a highway that have more frequent accidents so that determinations may be made whether the number of accidents for those portions may be reduced.

Figure 5:
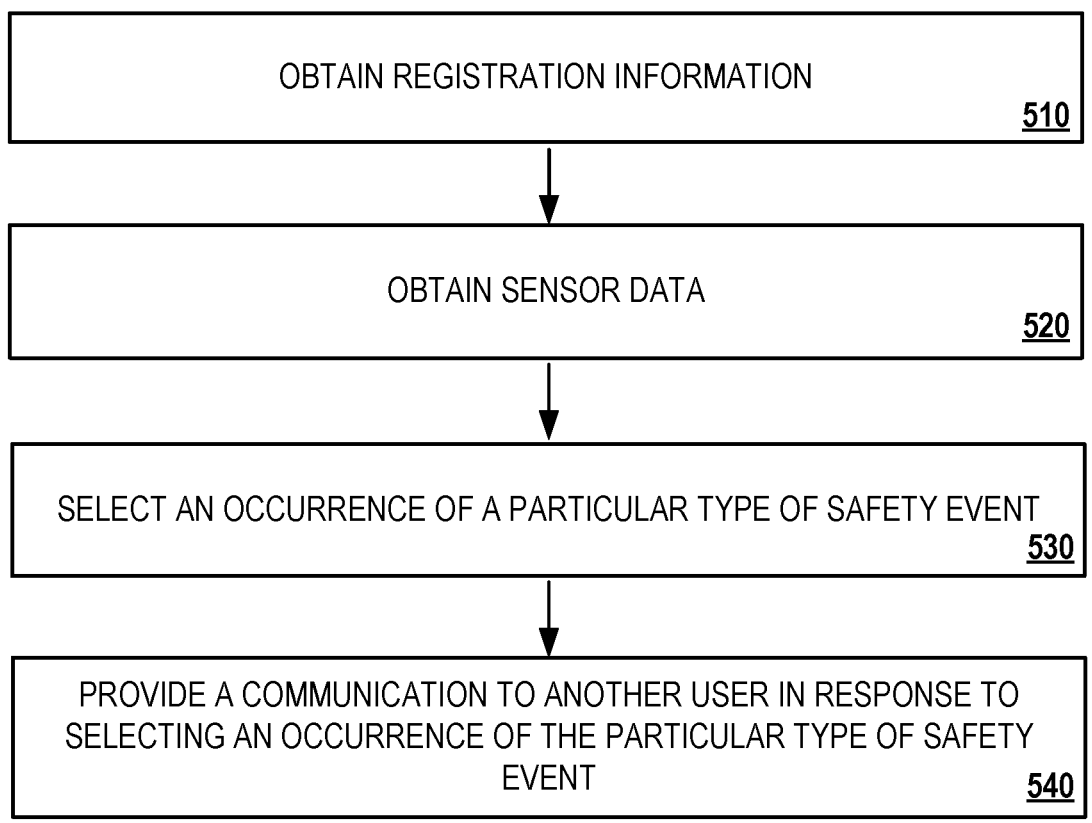
FIG. 5 illustrates an example of a process for providing communications indicating an occurrence of a particular type of safety incident experienced by a user.

FIG. 5 illustrates an example of a process 500 for providing communications indicating an occurrence of a particular type of safety incident experienced by a user. Briefly, the process 500 may include obtaining registration information (510), obtaining sensor data (520), selecting an occurrence of a particular type of safety incident (530), and providing communication to another user in response to selecting an occurrence of the particular type of safety incident (540).

In more detail, the process 500 may include obtaining registration information (510). For instance, the application server 180 may obtain registration information that indicates that safety devices 410A, 410B, and 410C are registered with the user 402. In some implementations, the registration information may be included in a user profile for the user that is stored within the stored historical data 424. In other implementations, the registration information may be transmitted from the mobile device 230.

The process 500 may include obtaining sensor data (520). For instance, the application server 180 may obtain sensor data from the safety devices 410A, 410B and 410C. As described above, the sensor data may include various types of information related to the present safety conditions of the user 402. For example, the sensor data may include biometric data indicating a physiological state of the user 402 (e.g., heart rate or blood pressure), accelerometer and/or gyroscope data indicating movement of the user 402 while performing a type of activity, or other types of data that may be used to determine if the user has experienced an occurrence of a safety incident.

The process 500 may include selecting an occurrence of a particular type of safety incident (530). For instance, the application server 180 may select an occurrence of a particular type of safety incident experienced by the user 402 from among a plurality of types of safety incidents that are included within the safety incident repository 424. The selection of the occurrence of the particular type of safety incident experienced by the user 402 may be based on the sensor data obtained from the safety devices 410A, 410B, and 410C, and/or the registration information that indicates that the safety devices 410A, 410B, and 410C are registered with the user 402. As described above, in some implementations, the application server 180 accesses the safety incident repository 422, which includes a list of different types of safety incidents and specifies different safety indicators associated with each type of safety incident. In such implementations, the application server 180 determines the satisfactions of conditions associated with the safety indicators based on the obtained sensor data, and then selects a particular type of safety incident from among the list of different types of safety incidents in order to select an occurrence of the particular type of safety incident experienced by the user 402.

The process 500 may include providing communication to another user in response to selecting an occurrence of the particular type of safety incident (540). For instance, in response to selecting the occurrence of the particular type of safety incident experienced by the user 402 from among the plurality of types of safety incidents included within the safety incident repository 424, the application server 180 may provide a communication to another user indicating the occurrence of the particular type of safety incident experienced by the user. Examples of users or entities that receive the communication may include law enforcement officers 404A, medical responders 404B, or authorized caretakers 404C. The communication may be selectively provided to another user based on, for example, the particular type of safety incident experienced by the user 402, the location of the safety incident, among other types of information that indicates whether another user will responsive to the safety incident experienced by the user 402.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed application-specific integrated circuits (ASICs).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A method performed by one or more computers, the method comprising:
   receiving, from a computing device carried by a user, data indicating (i) a current location of the computing device and (ii) that the user is travelling along a path;
   determining that the user has deviated from the path based on the current location;
   determining whether other users experienced safety incidents at the current location;
   based on determining that the user has deviated from the path and the other users experienced safety incidents at the current location, determining that the user has likely experienced a safety incident; and
   providing a communication to another user based on determining that the user has likely experienced the safety incident.

2. The method of claim 1, wherein based on determining that the user has deviated from the path and the other users experienced safety incidents at the current location, determining that the user has likely experienced a safety incident comprises:
    determining that the user has likely experienced the safety incident based on prior occurrences of safety incidents previously experienced by the user.

3. The method of claim 1, further comprising:
    based on determining that the user has deviated from the path and the other users experienced safety incidents at the current location, updating a user profile of the user to indicate occurrence of the safety incident.

4. The method of claim 1, wherein:
    the computing device is a wearable device configured to collect biometric data of the user; and
    the method further comprises accessing sensor data collected by a vehicle being operated by the user while traveling along the path; and
    determining that the user has likely experienced the safety incident comprises determining that the user has experienced the safety incident based at least on the sensor data collected by a vehicle.

5. The method of claim 1, wherein:
    the safety incident is associated with a condition that, once satisfied, indicates likely occurrence of the safety incident; and
    determining that the user has likely experienced a safety incident comprises determining that the condition for the safety incident has been satisfied based on sensor data collected by the computing device.

6. The method of claim 1, wherein providing the communication to another user comprises:
    determining one or more data types associated with sensor data collected by the computing device; and
    determining a second user to provide the communication based on the current location and the one or more data types.

7. The method of claim 1, wherein the another user comprises one or more of a law enforcement officer, an emergency medical technician, or an authorized caretaker for the user.

8. The method of claim 1, wherein the current location is determined based on global positioning system data collected by the computing device.

9. A system comprising:
    one or more computing devices; and
    one or more storage devices storing instructions that, when executed by the one or more computing devices, cause the one or more computing devices to perform operations comprising:
        receiving, from a computing device carried by a user, data indicating (i) a current location of the computing device and (ii) that the user is travelling along a path;
        determining that the user has deviated from the path based on the current location;
        determining whether other users experienced safety incidents at the current location;
        based on determining that the user has deviated from the path and the other users experienced safety incidents at the current location, determining that the user has likely experienced a safety incident; and
        providing a communication to another user based on determining that the user has likely experienced the safety incident.

10. The system of claim 9, wherein based on determining that the user has deviated from the path and the other users experienced safety incidents at the current location, determining that the user has likely experienced a safety incident comprises:
    determining that the user has likely experienced the safety incident based on prior occurrences of safety incidents previously experienced by the user.

11. The system of claim 9, wherein the operations further comprise:
    based on determining that the user has deviated from the path and the other users experienced safety incidents at the current location, updating a user profile of the user to indicate occurrence of the safety incident.

12. The system of claim 9, wherein:
    the computing device is a wearable device configured to collect biometric data of the user; and
    the operations further comprise accessing sensor data collected by a vehicle being operated by the user while traveling along the path; and
    determining that the user has likely experienced the safety incident comprises determining that the user has experienced the safety incident based at least on the sensor data collected by a vehicle.

13. The system of claim 9, wherein:
    the safety incident is associated with a condition that, once satisfied, indicates likely occurrence of the safety incident; and
    determining that the user has likely experienced a safety incident comprises determining that the condition for the safety incident has been satisfied based on sensor data collected by the computing device.

14. The system of claim 9, wherein providing the communication to another user comprises:
    determining one or more data types associated with sensor data collected by the computing device; and
    determining a second user to provide the communication based on the current location and the one or more data types.

15. The system of claim 9, wherein the another user comprises one or more of a law enforcement officer, an emergency medical technician, or an authorized caretaker for the user.

16. A non-transitory computer-readable storage device encoded with computer program instructions that, when executed by one or more computing devices, cause the one or more computing devices to perform operations comprising:
    receiving, from a computing device carried by a user, data indicating (i) a current location of the computing device and (ii) that the user is travelling along a path;
    determining that the user has deviated from the path based on the current location;
    determining whether other users experienced safety incidents at the current location;
    based on determining that the user has deviated from the path and the other users experienced safety incidents at the current location, determining that the user has likely experienced a safety incident; and
    providing a communication to another user based on determining that the user has likely experienced the safety incident.

17. The non-transitory computer-readable storage device of claim 16, wherein based on determining that the user has deviated from the path and the other users experienced safety incidents at the current location, determining that the user has likely experienced a safety incident comprises:

determining that the user has likely experienced the safety incident based on prior occurrences of safety incidents previously experienced by the user.

18. The non-transitory computer-readable storage device of claim 16, wherein the operations further comprise:
based on determining that the user has deviated from the path and the other users experienced safety incidents at the current location, updating a user profile of the user to indicate occurrence of the safety incident.

19. The non-transitory computer-readable storage device of claim 16, wherein:
the computing device is a wearable device configured to collect biometric data of the user; and
the operations further comprise accessing sensor data collected by a vehicle being operated by the user while traveling along the path; and
determining that the user has likely experienced the safety incident comprises determining that the user has experienced the safety incident based at least on the sensor data collected by a vehicle.

20. The non-transitory computer-readable storage device of claim 16, wherein:
the safety incident is associated with a condition that, once satisfied, indicates likely occurrence of the safety incident; and
determining that the user has likely experienced a safety incident comprises determining that the condition for the safety incident has been satisfied based on sensor data collected by the computing device.

* * * * *